United States Patent
Boren et al.

(10) Patent No.: US 6,410,719 B1
(45) Date of Patent: Jun. 25, 2002

(54) BLOOD GROUP ANTIGEN BINDING PROTEIN AND CORRESPONDING AGENTS

(75) Inventors: Thomas Boren, Törelvågen 68, S-906 28 Umeå; Anna Arnqvist, Umeå; Staffan Normark, Stockholm; Dag Ilver, Umeå, all of (SE)

(73) Assignee: Thomas Boren, Umea (SE)

( * ) Notice: Subject to any disclaimer, the term of this patent is extended or adjusted under 35 U.S.C. 154(b) by 0 days.

(21) Appl. No.: 09/021,560

(22) Filed: Feb. 10, 1998

Related U.S. Application Data

(63) Continuation of application No. PCT/SE97/01009, filed on Jun. 10, 1997.
(60) Provisional application No. 60/041,040, filed on Mar. 21, 1997.

(30) Foreign Application Priority Data

Jun. 10, 1996 (SE) ................................. 9602287
Mar. 19, 1997 (SE) ................................. 9701014

(51) Int. Cl.⁷ ............................................. C07H 21/04
(52) U.S. Cl. ..................... 536/23.7; 536/23.1; 514/44
(58) Field of Search ............................... 424/9.2, 256.1, 424/184.1, 185.1, 242.1, 94.5; 435/7.21, 172.1, 172.3, 240.2, 800.2, 69.1, 69.3, 70.1, 240.1; 935/59, 60, 70; 536/23.1, 23.7; 530/350; 544/44

(56) References Cited

U.S. PATENT DOCUMENTS 5,625,124 A * 4/1997 Falk et al. ..................... 800/2
5,807,732 A * 9/1998 Lowe et al. .................. 435/240.2
5,843,463 A * 12/1998 Krivan et al. ................ 424/256.1
6,033,663 A * 3/2000 Ketchem et al. .............. 424/94.5
6,096,521 A * 8/2000 Haas et al. ................... 435/70.1
6,238,894 B1 * 5/2001 Taylor et al. .................. 435/101

FOREIGN PATENT DOCUMENTS

WO        747646       * 12/1997

OTHER PUBLICATIONS

Reeck, G.R et al, Cell, vol. 50, p. 667, Aug. 28, 1987.*

Lewin, R. Science, vol. 237, p. 1570, 1987.*

Evans et al, Journal of Bacteriology, Feb. 1993, vol. 175(3), pp. 674–683, 1993.*

(List continued on next page.)

*Primary Examiner*—Lynette R. F. Smith
*Assistant Examiner*—Ginny Allen Portner
(74) *Attorney, Agent, or Firm*—Birch, Stewart, Kolasch & Birch, LLP

(57) ABSTRACT

A novel bacterial blood group antigen binding (BAB) adhesin protein was isolated and purified, whereby said protein or fractions thereof bind specifically to *Helicobacter pylori* fucosylated blood group antibodies. The protein sequence of said adhesin is disclosed in this application. Simultaneously the DNA sequences for two genes, babA and babB, producing highly similar proteins, are disclosed. Said adhesin and/or DNA is useful for diagnose and therapy and/or profylax directed against *H. pylori* induced infections, e.g. gastritis and acid peptic disease.

4 Claims, 21 Drawing Sheets

OTHER PUBLICATIONS

Huang et al, Journal of General Microbiology, vol. 138, pp. 1503–1513, 1992.*

Lelwala–Guruge et al, ZBL. Bakt. vol. 280, pp. 93–106, 1993.*

Chan et al, Glycobiology, vol. 5(7), pp. 683–688, 1995.*

Moran, Anthony P., FEMS Immunology and Medical Microbiology, vol. 10, pp. 271–280, 1995.*

Boren et al, Trends in Microbiology, vol. 2(7), Jul., 1994.*

Sherburne et al, Infection and Immunity, vol. 62(12), pp. 4564–4568, Dec. 1995.*

Boren et al, Science, vol. 262, pp. 1892–1895, 1993.*

Lelwala–Gruge et al, APMIS, vol. 100, pp. 908–913, 1992.*

Wadstrom, T, ACTA Microbiologica Hungarica, vol. 38 (3–4), pp. 164–165, 1991.*

Wadstrom, T et al, European Journal of Gastroenterology and Hepatology, vol. 5, S2, Oct., pp. S12–S15, 1993.*

Wadstrom, T et al, Aliment Pharmacol. Therapy, Apr., vol. 10, Suppl. 1, pp. 17–27, 1996.*

Orkin, Stuart H et al, NIH Report and Recommbendations of the Panel to assess the NIH investment in research on gene therapy, Dec. 7, 1995.*

Taylor et al, Journal of Bacteriology, Nov. 1992, vol. 174(21), pp. 6800–6802.*

Bukanov, N.O et al, Molecular Microbiology, Feb. 1994, pp. 509–523, vol. 11(3), Feb. 1994.*

Amano Kenichi, Akita Igaku (Akita Journal of Medicine), vol. 24(2), pp. 101–108, (English translation), 1997.*

Wirth, H et al, Infection Immunity, vol. 64(11), Nov. 1996, pp. 4598–4605, Nov. 1996.*

Simoons–Smit et al, Journal of Clinical Microbiology, vol. 34(9), pp. 2196–2200, Sep. 1996.*

Enders, G et al, Infection Immunity, vol. 63(7), pp. 2473–2477, Jul. 1995.*

Alkout, AH et al, Gut, Jul. 17–19, 1995, vol. 37(suppl. 7) p. A21, abstract 84.*

Odenbreit, S et al, Molecular Microbiology, vol. 20(2), pp. 361–373, Apr. 1996.*

* cited by examiner

FIGURE 6

```
      -23                      1
       ▼                       ▼
BabA  SKKEKKHILSLTLGSLLVSTLSAEDDGFYTSVGYQIGEAAQMVTNTKGIQ
      .|... .|||.|: |     |  ||||||||||||||||||||||||||
BabB  MKKNPFTLSLSLSFL....LHAEDDGFYTSVGYQIGEAAQMVTNTKGIQ
      ▲
      -18          41 43
                   ▼ ▼
      DLSDNYENLSKLLTRYSTLNTLIKLSADPSAINAARENLGASAKNLIGDT
      :||||||.|..||..||||||||||||||||||.||:|||.|||||::.
      QLSDNYEKLNNLLNNYSTLNTLIKLSADPSAINDARDNLGSSAKNLLDVK

79
      ▼
      KNSPAYQAVLLAINAAVGFWNVLGYATQCGGNANGQESTSSTTIFNNEPG
      .||||||||||:||||:|.| :||  ..|  :..:...::. .||| ||
      TNSPAYQAVLLALNAAVGLWQVTSYAFTACGPGSNESANGGIQTFNNVPG

YRSTSITCSLNRYKPGYYGPMSIENFKKLNEAYQILQTALNKGLPALKEN
      :.|.|||. . |.||. ||:|..|: |:|:||||:|    |:|.| ..|
      QKTTTITCN.SYYQPGHGGPISTANYAKINQAYQIIQ....KALTANEAN

NGTVSVTYTYTCSGEGNDNCSKKATGVSDQNGGTKTKTQTIDGKTVTTTI
      .:.|.|  .|.. : ....|:.|    ...|..|.   ||| : |
      GDGVPVLSDTTTKLDFTIQGDKRTGG....RPNTPKKFPWSDGKYIHT..

SSKVVDSQAKGNTTRVSYTEITNKLDGVPDSAQALLAQASTLINTINTAC
      . :|. :.:...|::              ...:.||.|| |||.:|.|:|.||
      ..QWIDTTPQSTETKI..........NTENNAQELLKQASIIITTLNEAC

PYFSVTNKSGGPQMEPTRGKLCG.FTEEISAIQKMITDAQELVNQTSVIN
      | |  .. ||   |   ...|.:|| |.:||||||  ||.:||| |.|..::.
      PNFQ.NGGSGYWQGISGNGTMCGMFKNEISAIQGMIANAQEAVAQSKIVS

339
                    ▼
      EHEQSTPVGGNNGKPFNPFTDASFAQGMLANASAQAKMLNLAHQVGQTIN
      |:.|. . . :.|||||||||||||:|| || |||.:|| .||..
      ENAQN.QNNLDTGKPFNPFTDASFAQSMLKNAQAQAEILNQAEQVVK...

418
                                                  ▼
      PDNLTGTFKNFVTGFLATCNNKSTAGTSGTQGSPPGTVTTQTFASGCAYV
      |:. .||||.: |:.|  :. .::.||.    || ||..|||||||||
      ..NFEKIPKNFVSDSLGVCYEEQGGERRGTN...PGQVTSNTFASGCAYV

EQTITNLNNSIAHFGTQEQQIQQAENIADTLVNFKSRYSELGNTYNSITT
      ||||||||||||||||||||||||||||||||||||||||||||||||||
      EQTITNLNNSIAHFGTQEQQIQQAENIADTLVNFKSRYSELGNTYNSITT

ALSKVPNAQSLQNVVGKKNNPYSPQGIETNYYLNQNSYNQIQTINQELGR
      ||||||||||||||||||||||||||||||||||||||||||||||||||
      ALSKVPNAQSLQNVVGKKNNPYSPQGIETNYYLNQNSYNQIQTINQELGR

NPFRKVGIVSSQTNNGAMNGIGIQVGYKQFFGQKRKWGARYYGFFDYNHA
      ||||||||||||||||||||||||||||||||||||||||||||||||||
      NPFRKVGIVSSQTNNGAMNGIGIQVGYKQFFGQKRKWGARYYGFFDYNHA

FIKSSFFNSASDVWTYGFGADALYNFINDKATNFLGKNNKLSVGLFGGIA
      ||||||||||||||||||||||||||||||||||||||||||||||||||
      FIKSSFFNSASDVWTYGFGADALYNFINDKATNFLGKNNKLSVGLFGGIA

LAGTSWLNSEYVNLATMNNVYNAKMNVANFQFLFNMGVRMNLARSKKKGS
      ||||||||||||||||||||||||||||||||||||||||||||||||||
      LAGTSWLNSEYVNLATMNNVYNAKMNVANFQFLFNMGVRMNLARSKKKGS

DHAAQHGIELGLKIPTINTNYYSFMGAELKYRRLYSVYLNYVFAY* 721
      ||||||||||||||||||||||||||||||||||||||||||||||
      DHAAQHGIELGLKIPTINTNYYSFMGAELKYRRLYSVYLNYVFAY* 689
``` babA

```
  1  TTTCAGTCAA GCCCAAAGCT ATGCGCAAAA CGCTTATGCT AAAGAGAATT
 51  TACAAGCACA GCCGTCCAAG TATCAAAACA GCGTGCCTGA AATCAATATT
101  GATGAAGAAG AAATCCCCTT TAAGGGTTAA AATTAAGGAG ACATTATGGA
151  AAGAAAACGC TATTCAAAAC GCTATTGCAA ATACACTGAA GCTAAAATCA
201  GCTTTATTGA CTATAAAGAT TTGGACATGC TCAAGCACAC GCTATCAGAG
251  CGCTATAAAA TCATGCCAAG GAGGTTGACA GGCAATAGCA AAAAGTGGCA
301  AGAGAGGGTG GAAGTTAGCG ATCAAAAGAG CCCGCCACAT GGCTTTAATC
351  CCCTACATTG TGGATAGGAA AAAAGTCGTG GATAGCCCTT TTAAACAGCA
401  CTGAATTTTT GATTAGGGCT AATAGGGGGC ATGCCTTTTA ATCTTGTTTA
451  ATCTTGGCTC TATTTTTGTT AAACATCGGT TATAAAAGCG TTAAAAGCAC
501  TTTTAAAAATC CAATTAAAAG CGTTCAAAAG TAACGCAAAA AATCAAAAAA
```

Fig. 7A

```
551   ATGACAAAAT TTTTAAGAAA ATGACAAAAA AAAAAAAAAC GCTTTATGCT
601   ATAATATTCC AAATACATTC TAATGCAAAT GCATTCTAAT GCAAATGTAT
                                                    ORF Start
                                                      |
651   AATGAATGTA TGAAATCCCT AATATTCAAT CCAATTTAA|T CCAAAAAGGA
701   GAAAAAACAC ATCCTTTCAT TAACTTTTAGG CTCGCTTTTA GTTTCCACTT
751   TGAGCGGCTGA AGACGACGGC TTTTACACAA GCGTAGGCTA TCAAATCGGT
801   GAAGCCGCTC AAATGGTAAC AAACACCAAA GGCATCCAAG ATCTTTCAGA
851   CAACTATGAA AACTTGAGCA AACTTTTGAC CCGATACAGC ACCCTAAACA
901   CCCTTATCAA ATTGTCCGCT GATCCGAGCG CGATTAACGC GGCACGTGAA
951   AATCTGGGCG CGAGCGCGAA GAACTTGATC GGCGATACCA AAAATTCCCC
1001  CGCCTATCAA GCCGTGCTTT TGGCGATCAA TGCGGGCGGTA GGGTTTTGGA
```

Fig. 7B

```
1051  ATGTCTTAGG CTATGCTACG CAATGCGGGG GTAACGCTAA TGGTCAAGAA
1101  AGCACCTCTT CAACCACCAT CTTCAACAAC GAGCCCAGGGT ATCGATCCAC
1151  TTCCATCACT TGCAGTTTGA ACAGGTATAA GCCTGGATAC TACGGCCCTA
1201  TGAGCATTGA AAATTTCAAA AAGCTTAACG AAGCCTATCA AATCCTCCAA
1251  ACGGCTTTAA ATAAAGGCTT ACCCGCGCTC AAAGAAAACA ACGGAACGGT
1301  CAGTGTAACC TACACCTACA CATGCTCAGG GGAAGGGAAT GATAACTGCT
1351  CGAAAAAAGC CACAGGTGTA AGTGACCAAA ATGGCGGAAC CAAAACTAAA
1401  ACCCAAAACCA TAGACGGCAA AACCGTAACC ACCACGATCA GTTCAAAAGT
1451  CGTTGATAGT CAGGCAAAAG GTAATACAAC AAGGGTGTCC TACACCGAAA
1501  TCACTAACAA ATTAGACGGT GTGCCTGATA GCGCTCAAGC GCTCTTGGCG
```

Fig. 7C

```
1551  CAAGCGGAGCA CGCTCATCAA CACCATCAAC ACGGCATGCC CGTATTTTAG
1601  TGTAACTAAT AAAAGTGGTG GTCCACAGAT GGAACCGACT AGAGGGAAGT
1651  TGTGCGGTTT TACAGAAGAA ATCAGCGGCGA TCCAAAAGAT GATCACAGAC
1701  GCGCAAGAGC TGGTCAATCA AACGAGCGTC ATTAACGAGC ATGAACAATC
1751  AACCCCGGTA GGCGGTAATA ATGGCAAGCC TTTCAACCCT TTCACGGACG
1801  CAAGCTTCGC TCAAGGCATG CTCGCTAACG CTAGTGCGCA AGCCAAAATG
1851  CTCAATCTAG CCCATCAAGT GGGGCAAACC ATTAACCCTG ACAATCTTAC
1901  CGGGACTTTT AAAAATTTTG TTACAGGCTT TTTAGCCACA TGCAACAACA
1951  AATCAACAGC TGGCACTAGT GGCACACAAG GTTCACCTCC TGGCACAGTA
2001  ACCACTCAAA CTTTCGCTTC CGGTTGCGCC TATGTGGAGC AAACCATAAC
```

Fig. 7D

```
2051  GAATCTAAAC AACAGCATCG CTCATTTTGG CACTCAAGAG CAGCAGATAC
2101  AGCAAGCTGA AAACATCGCT GACACTCTAG TGAATTTCAA ATCTAGATAC
2151  AGCGAATTAG GGAATACTTA TAACAGCATC ACTACTGCGC TCTCCAAAGT
2201  CCCTAACGCG CAAAGCTTGC AAAACGTGGT GGGAAAAAAG AATAACCCCT
2251  ATAGCCCGCA AGGCATAGAA ACCAATTACT ACTTGAATCA AAACTCTTAC
2301  AACCAAATCC AAAACCATCAA CCAAGAATTA GGGCGTAACC CCTTTAGGAA
2351  AGTGGGCATC GTCAGTTCTC AAAACCAACAA TGGTGCCATG AATGGGATCG
2401  GTATCCAGGT GGGCTACAAG CAATTCTTTG GGCAAAAAAG GAAATGGGGT
2451  GCAAGATACT ACGGCTTTTT TGATTACAAC CATGCGTTCA TTAAATCCAG
2501  CTTCTTCAAC TCGGCTTCTG ACGTGTGGAC TTATGGTTTT GGAGCGGACG
```

Fig. 7E

```
2551 CTCTTTTATAA CTTCATCAAC GATAAAGCCA CCAATTTCTT AGGCAAAAAC
2601 AACAAGCTTT CTGTGGGGCT TTTTGGCGGG ATTGCGTTAG CGGGCACTTC
2651 ATGGCTTAAT TCTGAATACG TGAATTTAGC CACCATGAAT AACGTCTATA
2701 ACGCTAAAAT GAACGTGGCG AACTTCCAAT TCTTATTCAA CATGGGAGTG
2751 AGGATGAATT TAGCCAGATC CAAGAAAAAA GGCAGCGATC ATGCGGCTCA
2801 GCATGGGCATT GAGTTAGGGC TTAAAATCCC CACCATTAAC ACGAACTACT
2851 ATTCCCTTTAT GGGGGCTGAA CTCAAATACC GCAGGCTCTA TAGCGTGTAT
                                       ORF Stop
                                          |
2901 TTGAATTATG TGTTCGCTTA CTAA|AAACTA AAAATCCTTT GTGGAACTCC
2951 CTTTTTAAGG GGTTTCTTTT AAAGCCTTTA TTTTTTTTTG GAGGGGTTTA
3001 ATTTTTTTGA AACCTTTGTT TTTGAATTCT CTTTTTAATG GGTTTCTTTT
     ΔΔΔΔΔΔΔΔΔΔΔΔΔΔΔΔΔΔΔΔΔΔΔΔΔΔΔΔΔΔΔΔΔΔΔΔΔΔΔΔΔΔΔΔΔΔΔΔΔΔΔΔ
```

Fig. 7F

```
         AAAAAAAAAAAAAAAAAAAAAAAAAAAAAAAAAAAAAAAA
3051  TTGAACTCTT TGTTTTGAAC TCCTTTTTTT GAACTCCCTT TTTTAAACCC
3101  TTTCTTTTTT AAAATTCTCT TTTTGGGGG GTTTGATGAA AAATCCTTTT
3151  TTAGCGTTTT GGTATTGGTT AGTGGAAAAC TTGATACTAA TTTAAGCGAT
3201  AGTTTTTAAA AAGTGCTTCT TTAATATAGG GGGTTTAAGT TGGTGATTAA
3251  AAGGGGGGAA TGGTTTCAAA GCGCTTCCTA TCCCTTTAAG AAAATAAAAT
3301  AAAACTTTAA TAAAAATGAGT TTTACAACAA AATGAGATCC
```

Fig. 7G babB

```
  1  CATTTGATCG CATTGGATTT CAAAGAAGGG CGTTTTGTGA AAGGCTTTGG
 51  TCAAGCTTAT GATATTTTAG GCGACAAAAT CGCTTATGTT GGGGGTAAAG
101  GCAACCCACA CAATTTCGCT CACAAGAAAT AAACTTTCTC ACCCATAAGG
151  GGCAAACGCC CCCAAAAGAG TGCTTTTTAA AGAGGTTAAG GCAAAATCAA
201  GCTCTTTAGT ATTTAATCTT AAAAAATACT AAAAGCCTTT TTATGGGCTA
251  ACACCACACA AAAAGCGTCA AAATCAAAAA AATGACAAAA TTTTCCCCAA
301  ATGACAAAAA AAAAAAAAAA CGATTTTATG CTATATTAAC GAAATCTTGT
351  GATAAGATCT TATTCTTTTA AAAGATTTAC CTAACCATTT TAATTTCAAG
                                  ORF Start
                                     |
401  GAGAAAAAC|AT GAAAAAAAAC CCTTTTACTC TCTCTCTCTC TCTCTCGTTT
```

Fig. 8A

```
451  TTGCTCCACG CTGAAGACGA CGGCTTTTAC ACAAGCGTAG GCTATCAAAT
501  CGGTGAAGCC GCTCAAATGG TAACCAACAC CAAAGGCATC CAACAGCTTT
551  CAGACAATTA TGAAAAGCTG AACAATCTTT TGAATAATTA CAGCACCCTA
601  AACACCCTTA TCAAATTATC CGCTGATCCG AGTGCGATTA ACGACGCAAG
651  GGATAATCTA GGCTCAAGTG CTAAGAATTT GCTTGATGTT AAAACCAACT
701  CCCCGGCCTA TCAAGCCGTG CTTTTAGCGT TGAATGCGGC GGTGGGGTTG
751  TGGCAAGTTA CAAGCTACGC TTTTACTGCT TGTGGTCCTG GCAGTAACGA
801  GAGCGCAAAT GGAGGTATCC AAACTTTTAA TAATGTGCCA GGACAAAAGA
851  CGACAACCAT CACTTGCAAT TCGTATTATC AACCAGGACA TGGTGGGCCT
901  ATATCCACTG CAAACTATGC AAAAATCAAT CAAGCCTATC AAATCATTCA
```

Fig. 8B

```
 951  AAAGGCTTTG ACAGCCAATG AAGCTAATGG AGATGGGGTC CCCGTTTTAA
1001  GCGACACCAC TACAAAAACTT GATTTCACTA TTCAAGGAGA CAAAAGAACG
1051  GGTGGCCGAC CAAATACACC TAAAAAGTTC CCATGGAGTG ATGGGAAATA
1101  TATTCACACC CAATGGATTG ACACAACACC ACAATCAACA GAAACAAAGA
1151  TCAACACAGA AAATAACGCT CAAGAGCTTT TAAAACAAGC GAGCATCATT
1201  ATCACTACCC TAAATGAGGC ATGCCCAAAC TTCCAAAATG GTGGTAGCGG
1251  TTATTGGCAA GGGATAAGCG GCAATGGGAC AATGTGTGGG ATGTTTAAGA
1301  ATGAAATCAG CGCTATCCAA GGCATGATCG CTAACGCGCA AGAAGCTGTC
1351  GCGCAAAGTA AAATCGTTAG TGAAAATGCG CAAAATCAAA ACAACTTGGA
1401  TACTGGAAAA CCATTCAACC CTTTCACGGA CGCTAGCTTC GCTCAAAGCA
```

Fig. 8C

```
1451  TGCTCAAAAA CGCTCAAGCC CAAGCAGAGA TTTTAAACCA AGCCGAACAA
1501  GTGGTGAAAA ACTTTGAAAA AATCCCTAAA AATTTTGTAT CAGACTCTTT
1551  AGGGGTGTGT TATGAAGAGC AAGGGGGTGA GCGTAGGGGC ACCAATCCAG
1601  GTCAGGTTAC TTCTAACACT TTCGCTTCCG GTTGCGCCTA TGTGGAGCAA
1651  ACCATAAACGA ATCTAAACAA CAGCATCGCT CATTTTGGCA CTCAAGAGCA
1701  GCAGATACAG CAAGCTGAAA ACATCGCTGA CACTCTAGTG AATTTCAAAT
1751  CTAGATACAG CGAATTAGGG AATACTTATA ACAGCATCAC TACTGCGCTC
1801  TCCAAAGTCC CTAACGCGCA AAGCTTGCAA AACGTGGTGG GAAAAAAGAA
1851  TAACCCCTAT AGCCCGCAAG GCATAGAAAC CAATTACTAC TTGAATCAAA
1901  ACTCTTACAA CCAAATCCAA ACCATCAACC AAGAATTAGG GCGTAACCCC
                                                                    ...
                                                                    ...

Fig. 8D
```

```
1951  TTTAGGAAAG TGGGCATCGT CAGTTCTCAA ACCAACAATG GTGCCATGAA
2001  TGGGATCGGT ATCCAGGTGG GCTACAAGCA ATTCTTTGGG CAAAAAAGGA
2051  AATGGGGTGC AAGATACTAC GGCTTTTTTG ATTACAACCA TGCCGTTCATT
2101  AAATCCAGCT TCTTCAACTC GGCTTCTGAC GTGTGGACTT ATGGTTTTGG
2151  AGCGGACGCT CTTTATAACT TCATCAACGA TAAAGCCACC AATTTCTTAG
2201  GCAAAAACAA CAAGCTTTCT GTGGGGCTTT TTGGCGGGAT TGCGTTAGCG
2251  GGCACTTCAT GGCTTAATTC TGAATACGTG AATTTAGCCA CCATGAATAA
2301  CGTCTATAAC GCTAAAATGA ACGTGGCGAA CTTCCAATTC TTATTCAACA
2351  TGGGAGTGAG GATGAATTTA GCCAGATCCA AGAAAAAAGG CAGCGATCAT
2401  GCGGCTCAGC ATGGCATTGA GTTAGGGCTT AAAATCCCCA CCATTAACAC
      ΔΔΔΔΔΔΔΔΔΔΔΔΔΔΔΔΔΔΔΔΔΔΔΔΔΔΔΔΔΔΔΔΔΔΔΔΔΔΔΔΔΔΔΔΔΔΔΔ
```

Fig. 8E

```
2451  GAACTACTAT TCCTTTATGG GGGCTGAACT CAAATACCGC AGGCTCTATA
                                                            AAAAAAAAAA
                                                            AAAAAAAAAA
                                                            AAAAAAAAAA
                                       ORF Stop
                                          |
2501  GCGTGTATTT GAATTATGTG TTCGCTTACT AG|AAACTAAA AATCCTTTGT
2551  GGAACTCCCT TTTTAAGGGG TTTCTTTTAA AGCCTTTATT TTTTTTTGGA
2601  GGGGTTTAAT TTTTTTGAAA CCTTTGTTTT TGAATTCTCT TTTTAATGGG
2651  TTTCTTTTTT GAACTCTTTG TTTTGAACTC CTTTTTTTGA ACTCCCTTTT
2701  TTAAACCCTT TCTTTTTTAA AATTCTCTTT TTTGGGGGGT TTGATGAAAA
2751  ATCCTTTTTT AGCGTTTTGG TATTGGTTAG T
```

Fig. 8F

BLOOD GROUP ANTIGEN BINDING PROTEIN AND CORRESPONDING AGENTS

This application is a Continuation of PCT International Application No. PCT/SE97/01009 filed on Jun. 10, 1997, which designated the United States now providing U.S. national application No. 09/202,178 the entire contents of which are hereby incorporated by reference. This application also claims benefit under 35 U.S.C. § 119(e) of Provisional Application No. 60/041,040 filed on Mar. 21, 1997, the entire contents of which are hereby incorporated by reference.

FIELD OF THE INVENTION

The present invention relates to materials and methods for prevention, treatment and diagnosing of infections caused by *Helicobacter pylori*. More specifically the present invention relates to polypeptides and antibodies useful in vaccines for the treatment and prevention of pathologic infections caused by *Helicobacter pylori* strains. The present invention specifically relates to a bacterial blood group antigen binding adhesin (BAB-adhesin). The present invention further relates to polynucleotides useful for the recombinant production of said polypeptides and for use in immunization therapies. In addition, it relates to polypeptides, antibodies, and polynucleotides used for the detection of said bacteria.

BACKGROUND OF THE INVENTION

*Helicobacter pylori* is a causative agent for acid peptic disease and the presence of this organism is highly correlated to the development of gastric adenocarcinoma. Bacterial adherence to the human gastric epithelial lining was recently shown to be mediated by fucosylated blood group antigens.

The foregoing makes the prevention, diagnosing and treatment of *H. pylori* infections an urgent task. Further, the fact that developing countries frequently lack the resources for conventional treatment of gastric ulcers further underlines the importance of finding new ways of diagnosing, treatment and prevention of *H. pylori* induced infections. It is obvious, for many reasons, that disease prevention with vaccines is a preferable mode. A vaccine would provide an easily administered and economical prophylactic regimen against *H. pylori* infections. An effective vaccine against *H. pylori* is nevertheless presently lacking.

STATE OF THE ART

*H. pylori* colonizes the human gastric mucosa, in an equilibrium between adherence to the epithelial surface mucous cells and the mucous layer lining the gastric epithelium. Once infected, bacteria seems to colonize for a lifetime (Blaser, 1993; Borén and Falk, 1994). Attachment to the epithelial lining protects the bacteria from the antimicrobial effects of the acidic gastric juice of the stomach lumen, as well as from physical forces such as peristalsis. For survival in this hostile ecological niche, *H. pylori* has developed a battery of virulence factors; such as production of the enzyme urease (Labigne et al., 1991; Eaton and Krakowka, 1994), that buffers the micro environment around the bacteria and the polar flagellae (Eaton et al., 1992) to ensure high motility, a prerequisite in an ecological niche where the turnover of the mucous layer is in the range of hours. A subset of *H. pylori* strains produces the vacuolating cytotoxin, VacA (Cover et al., 1994, Phadnis et al., 1994; Schmitt and Haas, 1994; Telford et al., 1994), and the cytotoxin associated antigen CagA (Covacci et al., 1993).

Attachment is essential for colonization of the epithelial lining and bacteria express surface associated adhesion molecules that recognize specific carbohydrate or protein receptors on the cell surfaces or mucous lining. The specificity in this interaction in combination with the genetically regulated receptor distribution results in a restricted range of cell lineages and tissues available for colonization. Several putative receptor structures have been described for *H. pylori*, such as the hemagglutinin-sialic acid (Evans et al., 1988), sulphated glycoconjugates (Ascencio et al., 1993) and sulphatides (Saitoh et al., 1991; Kamisago et al., 1996). Recently, the fucosylated blood group antigens H-1 and Lewis$^b$ were described (Borén et al., 1993), mediating specific adherence of *H. pylori* to human and rhesus monkey gastric surface mucous cells in situ. The H-1 and Lewis$^b$ antigens are part of the blood group antigens that define blood group O in the ABO system.

Surface-exposed proteins are not seldom constituents of the outer membrane. The outer membrane has a structural role and acts as a selective barrier, determining what enters the cell and what molecules are secreted. One class of outer membrane proteins are called porins, and create hydrophilic pores through the outer membrane where specific metabolites, such as sugar molecules, can cross. Trust and co-workers reported recently about the finding of a number of outer membrane proteins in *H. pylori* which were suggested to constitute a family of porin proteins (Exner et al., 1995).

The BAB adhesin has previously been identified and shown to be localized on the bacterial surface of *H. pylori* (SE 9602287-6). The blood group binding activity was shown to be pH dependent and the present inventors present evidence that the binding affinity to the Lewis$^b$ receptor reveals a high equilibrium constant. For the purification of the BAB adhesin, a crosslinker labelled receptor conjugate was used in order to mediate specific transfer of biotin to the adhesins on the bacterial surface. Thereafter the biotin-labelled adhesin could be extracted by streptavidin coated magnetic beads. Determination of the amino terminal amino acid sequence of the purified BAB adhesin exhibit homologies to outer membrane proteins of *H. pylori* porins.

THE OBJECTIVE OF THE PRESENT INVENTION

The objective of the present invention was to further purify and characterize the *H. pylori* blood group antigen binding (BAB) adhesin to make possible the development of methods and materials for specific and selective diagnosing and treatment of *H. pylori* induced infections and related diseases and the development of said methods and materials. A further and equally important objective was to determine the DNA sequences of the genes involved in the expression of this protein. The objective was fulfilled through the protein disclosed the DNA disclosed and the methods and materials disclosed. The DNA sequences are attached as SEQ. ID NOS. 1 and 3 disclosing the babA and babB sequences, respectively. The full protein sequence is disclosed in SEQ ID NOS. 2 and 4.

DESCRIPTION OF THE FIGURES

FIG. 6 shows the alignment of the amino acid sequences of BabA and BabB (SEQ ID NOS:2 and 4).

FIG. 7 shows the nucleic acid sequence of SEQ ID No 1, and the start and stop positions of the encoded open reading frame (ORF).

FIG. 8 shows the nucleic acid sequence of SEQ ID No 3, and the start and stop positions of the encoded open reading frame (ORF).

DESCRIPTION OF THE INVENTION

Figure 1A:
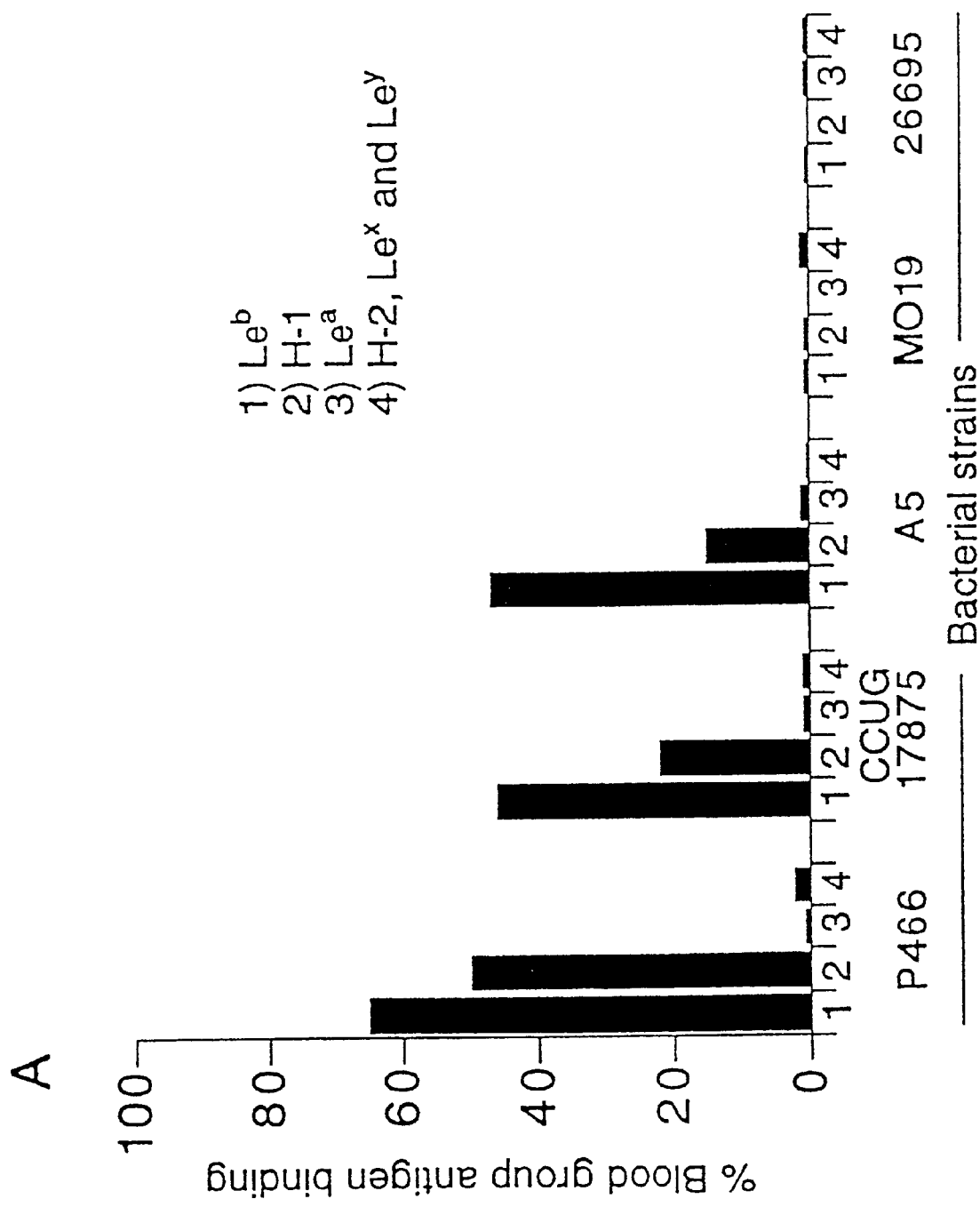
FIG. 1A–C) illustrates the bacterial binding to soluble blood group antigens. *H. pylori* strains were incubated with $^{125}$I-labeled blood group antigene glycoconjugates and bound $^{125}$I-activity was measured (Note the absence of blood group antigen binding shown for strains MO19 and 26695.), B) illustrates an receptor displacement assay. Strain CCUG 17875 was first incubated with 10 ng $^{125}$I-labeled Le$^b$ antigen glycoconjugate and the complex was then challenged (1 h) with an excess of unlabeled Le$^b$ or Le$^a$ glycoconjugate, before the $^{125}$I-activity in the bacterial pellet was measured. Concentrations of the unlabeled glycoconjugate ranged from 50 ng to 8 μg and FIG. C) shows the results of a Scatchard analysis of the *H. pylori*-Le$^b$ antigen interaction. Bacterial binding to the Le$^b$ glycoconjugate was titrated to an affinity constant (Ka) value of 8×10E10 M-1 (13).

The blood group antigen binding adhesin, BabA, has now been biochemically characterized and purified by a novel technique, receptor Activity Directed Affinity Tagging (Retagging). Two genes, babA and babB were found to code for two different but very similar proteins. The present invention thus comprises a novel blood group antigen binding adhesin. The DNA sequences are disclosed in SEQ. ID. No. 1 (babA) and SEQ. ID No. 3 (babB). The protein sequences are disclosed in FIG. 6. The invention also includes any pharmaceutical composition comprising said adhesin protein and/or fractions thereof. Examples of such pharmaceutical compositions are for example medicaments for the prevention or treatment of *Helicobacter pylori* induced gastritis, gastric and duodenal ulcers and gastric adenocarcinom. Optionally said pharmaceutical composition additionally encompasses pharmaceutically acceptable excipients.

Further the present invention comprises the BAB-adhesin gene or genes for express-ion of an adhesin protein according to the invention. Said invention also comprises a novel method for the isolation and purification of said adhesin. The disclosed genes are contemplated to function as a cassette system, the organism alternating between these to avoid immunity in the host. It is very likely, that homologies of the disclosed sequences exist and additionally supplement said cassette function in other strains of *H. pylori*. Also genes, starting with a homology of the first 70 amino acids or genes, ending with a homology of the last, about 300 amino acids, can function to this effect.

The invention additionally comprises monospecific antisera produced using the novel adhesin protein and/or/ fractions thereof. Said monospecific antisera is preferably produced according to any suitable, conventional method for producing monospecific antisera in vitro or in vivo, e.g. by inoculating a suitable mammal. Such methods are familiar to a person skilled in the art. Antibodies raised in a suitable mammal or in the patient to be treated, can subsequently be administered locally, e.g. orally to the patient.

The invention further comprises the use of said monospecific antisera for the manufacturing of a test kit for quantitative or qualitative determinations of adhesin protein or fractions thereof in cells, tissues or body fluids.

The invention further comprises the use of said adhesin protein or corresponding DNA for use in therapy or immunisation and/or in the manufacture of compositions for said uses. The invention specifically encompasses the use of said DNA for immunization therapy and for the manufacture for compositions for such therapy. Preferably, in an immunization therapy where said composition is administered orally to a patient, the adhesin protein, fractions thereof or said DNA is administered in combination with a pharmaceuticaly suitable immunostimulating agent. Examples of such agents include, but are not limited to the following: cholera toxin and/or derivatives thereof, heat labile toxins, such as coli toxin and similar agents. The composition according to the present invention can further include conventional and pharmaceutically acceptable adjuvants, familiar to a person skilled in the art of immunization therapy. Preferably, in an immunization therapy using the inventive DNA or fractions thereof, said DNA is preferably administered intramusculary, whereby said DNA is incorporated in suitable plasmide carriers. An additional gene or genes encoding a suitable immunostimulating agent can preferably be incorporated in the same plasmide.

Said immunization therapies are not restricted to the above described routes of administration, but can naturally be adapted to any one of the following routes of administration: oral, nasal, subcutaneous and intramuscular. Specially the oral and nasal methods of administration are promising, specially for large scale immunizations.

EXAMPLES

*H. pylori* strain CCUG 17875 was obtained from CCUG, Göteborg, Sweden. Strain A5, a gastric ulcer isolate, camed from Astra Arcus, Södertälje, Sweden. Strains P466 and M019 were described previously (Boren et. al, 1990). Strain 26695 came from Dr. K. A. Eaton, The Ohio State University and its genome was recently sequenced by TIGR, Rockville, Md., USA. The panel of 45 *H. pylori* clinical isolates came from the University Hospital in Uppsala, Sweden. Bacteria were grown at 37° C. in 10% CO2 and 5% O2 for 48 h.

All blood group antigen glycoconjugates used, i.e. semi-synthetic lycoproteins constructed by the conjugation of purified fucosylated oligosacharides to serum albumin (Boren et al., 1990, Rye, 1996) were from IsoSep AB, Tullinge, Sweden. The RIA was performed according to Falk et al. (1994) with some modifications; the H-1, Le$^b$, Le$^a$, H-2, Le$^x$ and Le$^y$ glycoconjugates were 125I-labeled by the Chloramine T method. 1 ml of bacteria (A600=OD 0.10) was incubated with 300 ng of 125I -labeled conjugate (i.e. an excess of receptors) for 30 min. in phosphate buffered saline (PBS), 0.5% albumin, 0.05% Tween-20 (BB-buffer). After centrifugation, 125I-activity in the bacterial pellet was measured by gamma scintillation counting.

In this study the present inventors first biochemically characterized and identified the *H. pylori* blood group antigen binding adhesin, BabA. *H. pylori* strains were analyzed for binding to soluble $^{125}$I-labeled fucosylated blood group antigens (FIG. 1A) (8, 9). Binding of these strains to the soluble blood group antigens correlate with adherence in situ (7, 5). The prevalence of blood group antigen binding (BAB)-activity was assessed among 45 clinical *H. pylori* isolates and the majority of the isolates, 71%, express Le$^b$ antigen binding properties (data not shown). In contrast, none of the reference strains (FIG. 1A), or strains from the panel of 45 clinical isolates, bind to the Le$^a$,H-2, Le$^x$, or Le$^y$ antigens (8). These results support our previous findings of high receptor specificity for the Le$^b$ and H-1 blood group antigens and demonstrate the high prevalence of BAB activity among clinical isolates.

Based on the presence or absence of virulence factors such as the Cytotoxin associated gene A (CacA) and the Vacuolating cytotoxin A (VacA), *H. pylori* strains are classified as type I or type II strains. *H. pylori* isolates from patients with duodenal ulcers most often express the VacA and the CagA-proteins, i.e. type-I strains (10). By definition, type U strains express neither markers. Twenty-one clinical isolates previously defined for expression of CagA and VacA (12) were analyzed for Le$^b$ antigen binding properties. Expression of CagA was found to correlate with bacterial binding to the Le$^b$ antigen (Table 1). The cagA gene belongs to a 40 kb pathogenicity island that encodes components of secretion and transport systems (11). These findings could indicate functional crosstalk between the cag pathogenicity island and the BabA adhesin gene, for the correct presentation of the BabA adhesin protein in the bacterial outer membrane.

TABLE 1

BAB activity among *H. pylori* Type I and Type II strains

| Type | Strain | BAB activity |
|---|---|---|
| Type I | CCUG 17874 | − |
| CagA$^+$, VacA$^+$ | G39 | − |
|  | G11 | − |
|  | G20 | − |
|  | G27 | + |
|  | G56 | + |
|  | G106 | − |
|  | G109 | + |
|  | 932 | + |
|  | Ba185 | + |
|  | 87A300 | + |
| Type Ia | 931 | + |
| CagA$^+$, VacA$^-$ | Ba99 | + |
|  | Ba179 | + |
|  | Ba194 | + |
| Type Ib | G12 | − |
| CagA$^-$, VacA$^+$ |  |  |
| Type Id | G104 | − |
| ΔcagA, VacA$^+$ | Tx30 | − |
| Type II | G21 | − |
| CagA$^-$, VacA$^-$ | G50 | − |
|  | G198 | − |

Figure 1B:
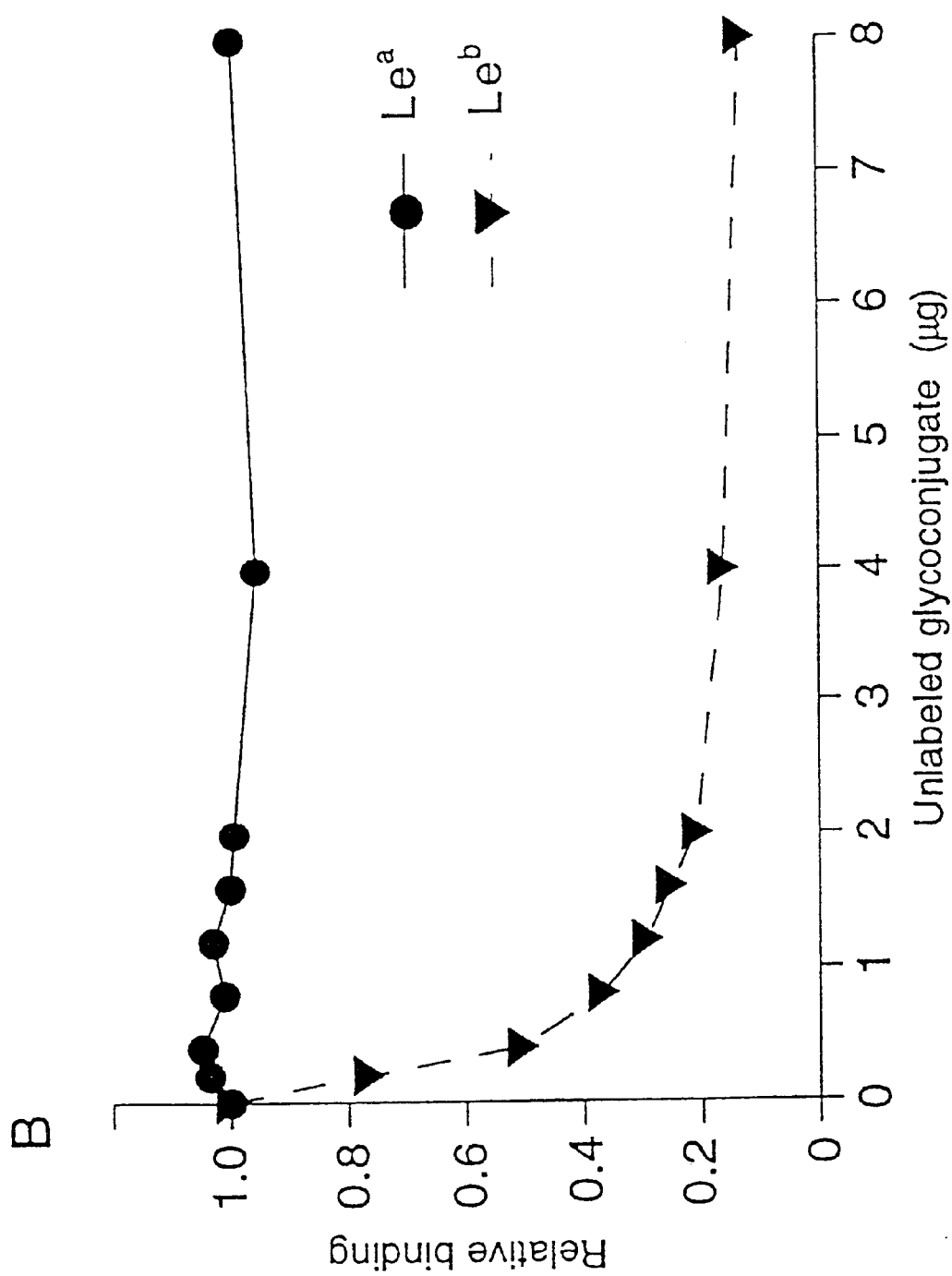
Figure 1C:
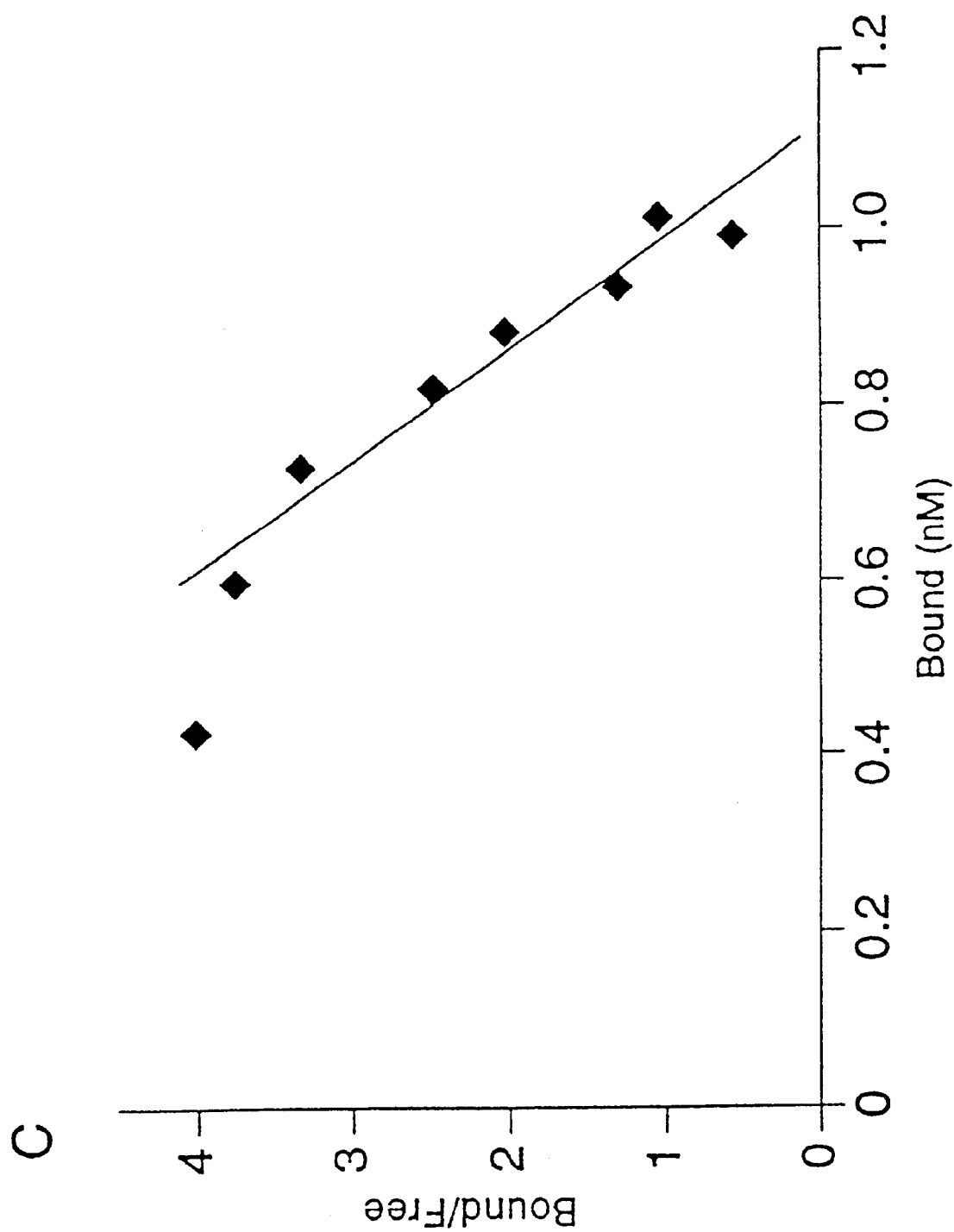

To further characterize BabA, the present inventors determined the affinity constant ($K_a$) between BabA and the Le$^b$ antigen. Since $K_a$-values are based on equilibrium conditions (13), the present inventors first analyzed the interaction by performing receptor displacement analysis. *H. pylori* CCUG 17875 (positive for Le$^b$ binding, FIG. 1 A) was first incubated with $^{125}$I-labeled Le$^b$ glycoconjugate. Then unlabeled Le$^b$ glycoconjugate was added in a dilution series. The unlabeled Le$^b$ conjugate displaced the bound $^{125}$I-labeled Le$^b$ glycoconjugate efficiently (FIG. 1B). The results demonstrate that the receptor-adhesin complex formed is in a true state of equilibrium. An equivalent excess of Le$^a$ glycoconjugate did not dissociate the Le$^b$-BabA complex, verifying the high receptor specificity (FIG. 1B). The $K_a$-value for the Le$^b$-BabA complex of strain CCUG 17875 was titrated with Le$^b$ glycoconjugate in concentrations from 10 ng to 260 ng/mL and determined to be of an high affinity close to $1 \times 10^{10} M^{-1}$ (FIG. 1C). The number of Le$^b$ glycoconjugate molecules bound to BabA on the bacterial cell surface was calculated to be around 500 per cell. This number is similar to the number or fimbriae organelles on the surface of *E. coli* (14). However, for the BabA adhesin, the calculations are based on the assumption that the majority of bacterial cells in the experiment exhibit an equal number of adhesin molecules with Le$^b$ antigen binding properties.

Figure 2:
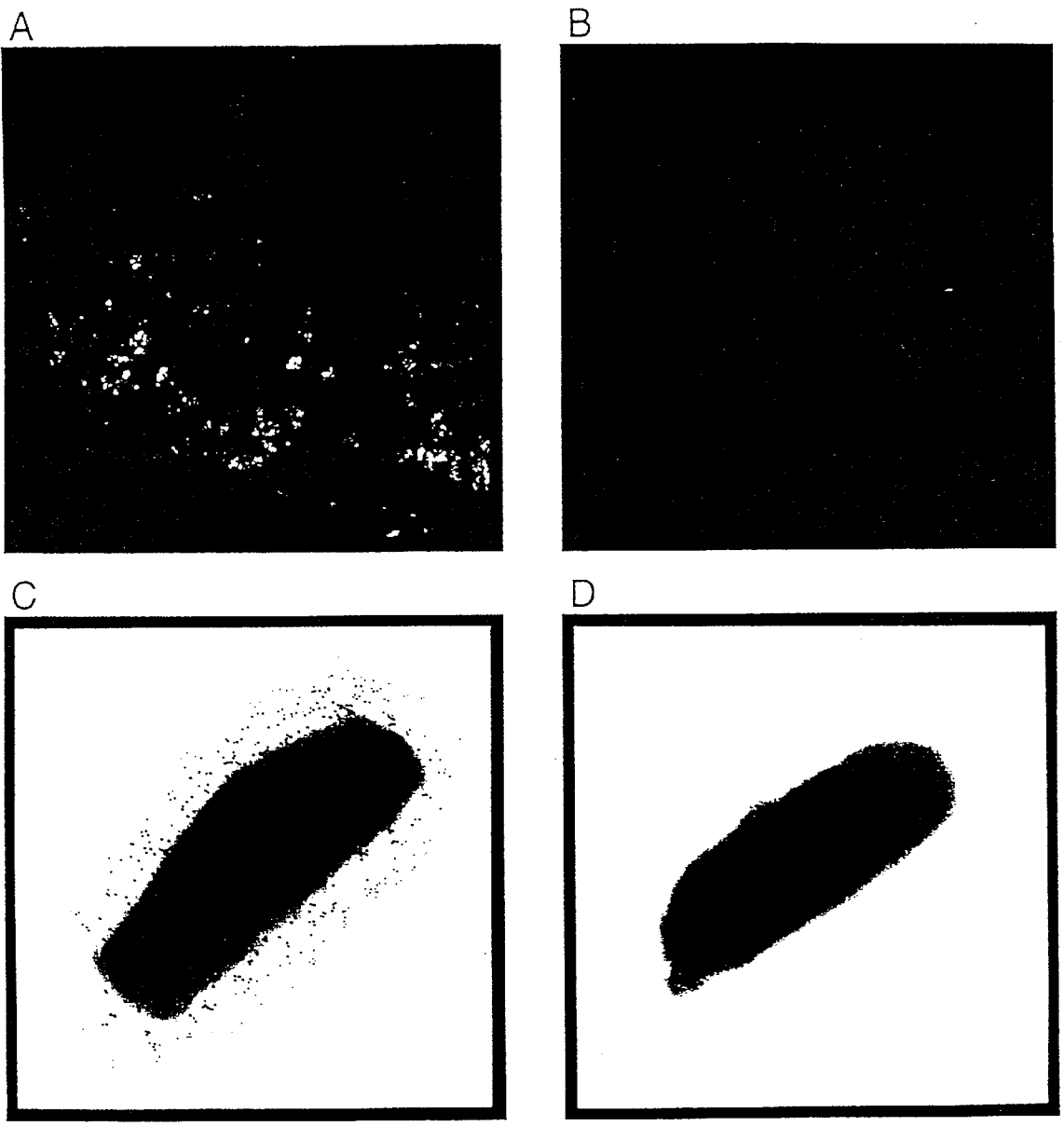
FIG. 2A–D Upper panel Prevalence of the BabA adhesin in the bacterial population. Cells of strain CCUG 17875 were incubated with biotinylated Le$^b$ (A) or Le$^b$ (B) glycoconjugate. Bound biotinylated Lewis-conjugate was detected with FITC-labeled streptavidin (green fluorescence) and bacteria were counterstained with propidium iodine (red fluorescence). Lower panel Localization of the BabA adhesin. For electron microscopy (15) cells of strain CCUG 17875 were incubated with biotinylated Le$^b$ (C) or Le$^a$

To determine the prevalence of BabA in the bacterial population, strain CCUG 17875 was incubated with Le$^b$ or Le$^a$ antigens, and bacterial binding activity was visualized by confocal fluorescence microscopy (15) (FIG. 2, upper panel). The analyses demonstrate the high prevalence of BabA binding activity in the bacterial population to the Le$^b$ antigen (FIG. 2A, green staining) and the complete lack of binding to the Le antigen (FIG. 2B, red counter staining).

Next, the localization and density of BabA on the bacterial cell surfaces was investigated by immunogold electron microscopy. The Le$^b$ antigen binding activity of the adhesin localized gold particles to the bacterial outer membrane (FIG. 2C) (15). Individual bacterial cells exhibit an equal number of gold particles (data not shown). When the Le$^b$ antigen was substituted with the Le$^a$ antigen (lacking receptor activity), no gold particles were detected (FIG. 2D).

The molecular weight of BabA was characterized by receptor overlay analysis. A protein extract of strain CCUG 17875 was separated on SDS-PAGE and blotted to a membrane. The membrane was incubated with biotinylated Le$^b$ glycoconjugate, followed by detection with streptavidin and enhanced chemiluminescence. The BabA adhesin activity corresponds to a single 74 kDa band (FIG. 3A). The 40 kDa band is presumably endogenous peroxidase activity since it stains independently of the Le$^b$ conjugate overlay (lane 3). BabA was very heat stable and could regain some activity after heating to 97° C. (FIG. 3A, lane 2). The panel of strains exhibited the same molecular weight of BabA (FIG. 3B).

Figure 4:
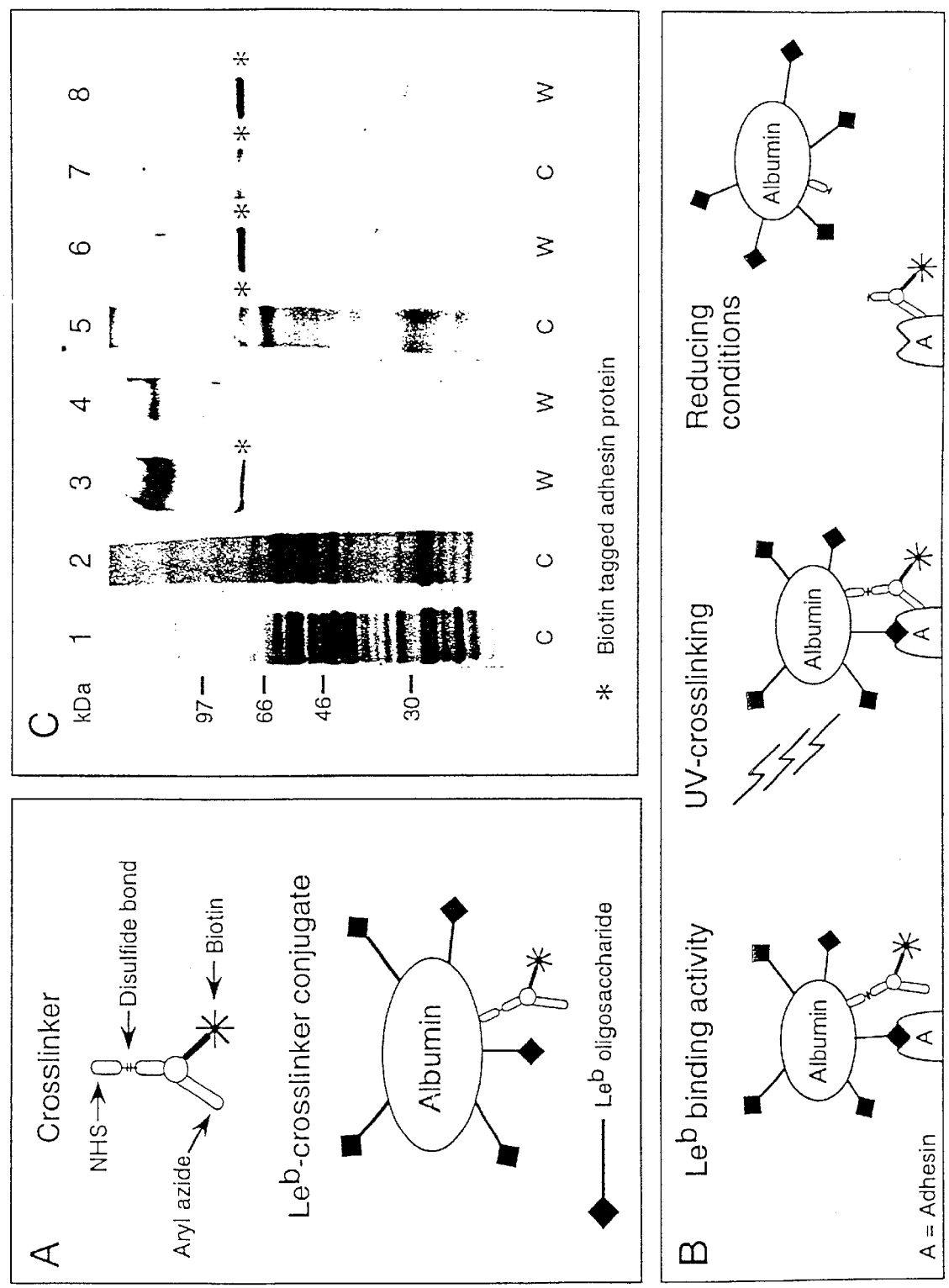
FIG. 4–C shows receptor activity directed affinity tagging and protein purification of the BabA adhesin.

To purify BabA, a novel technique was developed, Receptor Activity Directed Affinity Tagging (ReTagging). Multi-functional crosslinking agents with radiolabeled donating tags have been previously used for receptor-ligand characterization studies (16). However, the use of affinity donating tags, such as biotin residues presented on flexible spacer structures, adds a new dimension to the applicability of crosslinker technology. An affinity tag, biotin, is transferred to the adhesin protein by the receptor activity and is used for further identification and for affinity purification of the adhesin part of the interaction, by streptavidin (FIG. 4A, B).

A multi-functional crosslinking agent with a biotin donating handle was attached to the Le$^b$ glycoconjugate. The receptor activity of the Le$^b$ glycoconjugate subsequently directed the targeted biotin tagging of the BabA adhesin protein (FIG. 4A, B). After crosslinking, the bacterial protein from strains A5, P466, and CCUG 17875 were separated on SDS-PAGE. Immunodetection with streptavidin demonstrated a biotin tagged protein, with the molecular weight of 74 kDa (FIG. 3C) (28), These results support the estimates of the molecular weight from the previous overlay analyses (FIG. 3B). Strain MO19 devoid of Le$^b$ antigen binding properties (FIG. 3B) (FIG. 1A), was negative for binding also in this set of analyses (FIG. 3C).

Figure 5:
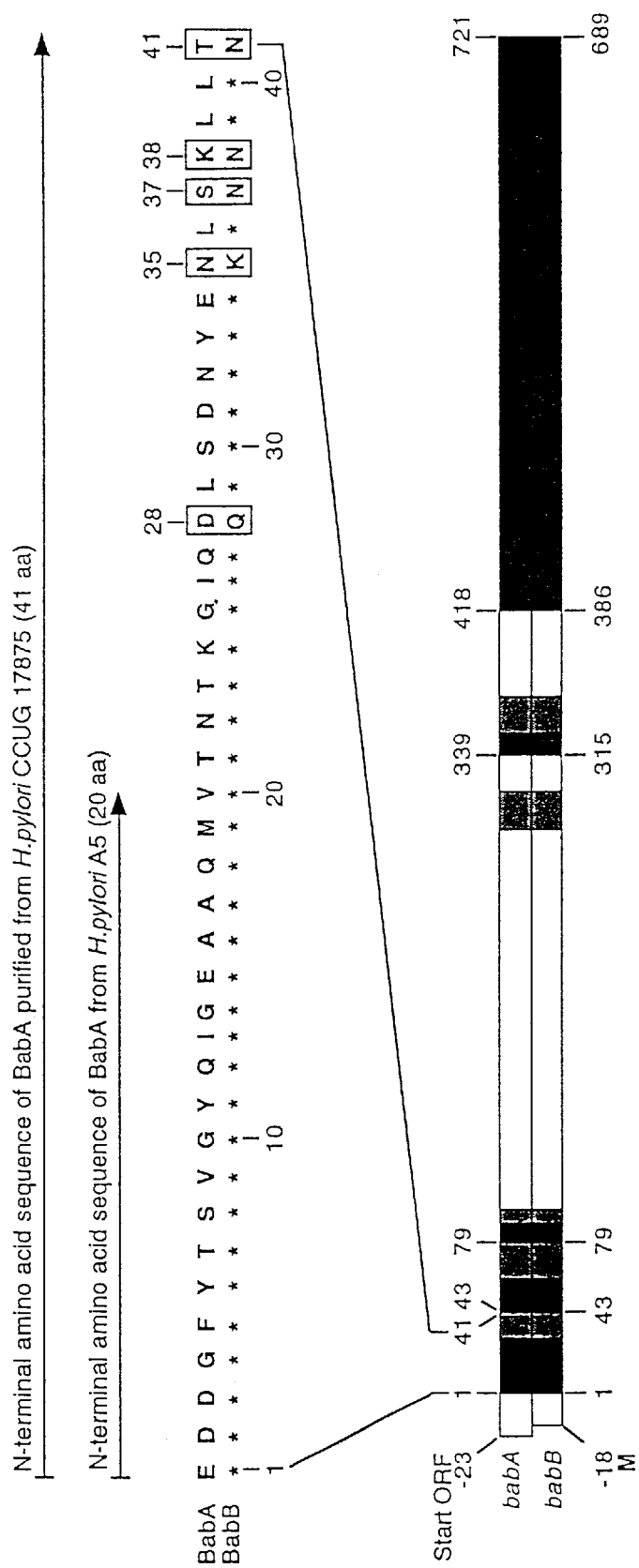
FIG. 5 shows the translated aminoacid sequence for the babA gene residues 1–48 of SEQ ID No. 2, corresponding to the N-terminal domain of the BabA adhesin.

The high specificity in the ReTagging technique provided a method for purification of the adhesin protein. Strains CCUG 17875 and A5, that both express the BabA adhesin (FIG. 1A) were processed by the ReTagging technique using crosslinker labeled Le$^b$ receptor conjugate as the biotin donor. After crosslinking, bacteria were suspended in SDS sample buffer. Streptavidin coated magnetic beads were subsequently added to the solubilized proteins, and biotin tagged BabA was extracted (FIG. 4C). The N-terminal 20 amino acid sequences of the BabA adhesins from strains CCUG 17875 (Australia) and A5 (Sweden) were found to be identical, indicating a biologically conserved protein (FIG. 5). Recently, a series of outer membrane proteins from *H. pylori* were characterized. These proteins, HopA-E, are homologous in their N-terminal sequences to BabA (17), possible indicating a motif for a common secretion mechanism. The biotin tagged BabA adhesin was purified more than 3000-fold from the cell extract, and the yield was calculated to 20%. However, based on data from the Scatchard plots, the level of available BabA adhesin would be about 5-times higher, i.e. approximately 1 mg adhesin/750 mg bacterial protein, which nevertheless could be the reason for the high signal to noise ratio (FIG. 3B). The purification of BabA via the ReTagging technique indicates the potential of this technique for the purification of lectins in complex receptor-ligand interactions, such as the selectin family of cell adhesion molecules.

Figure 3:
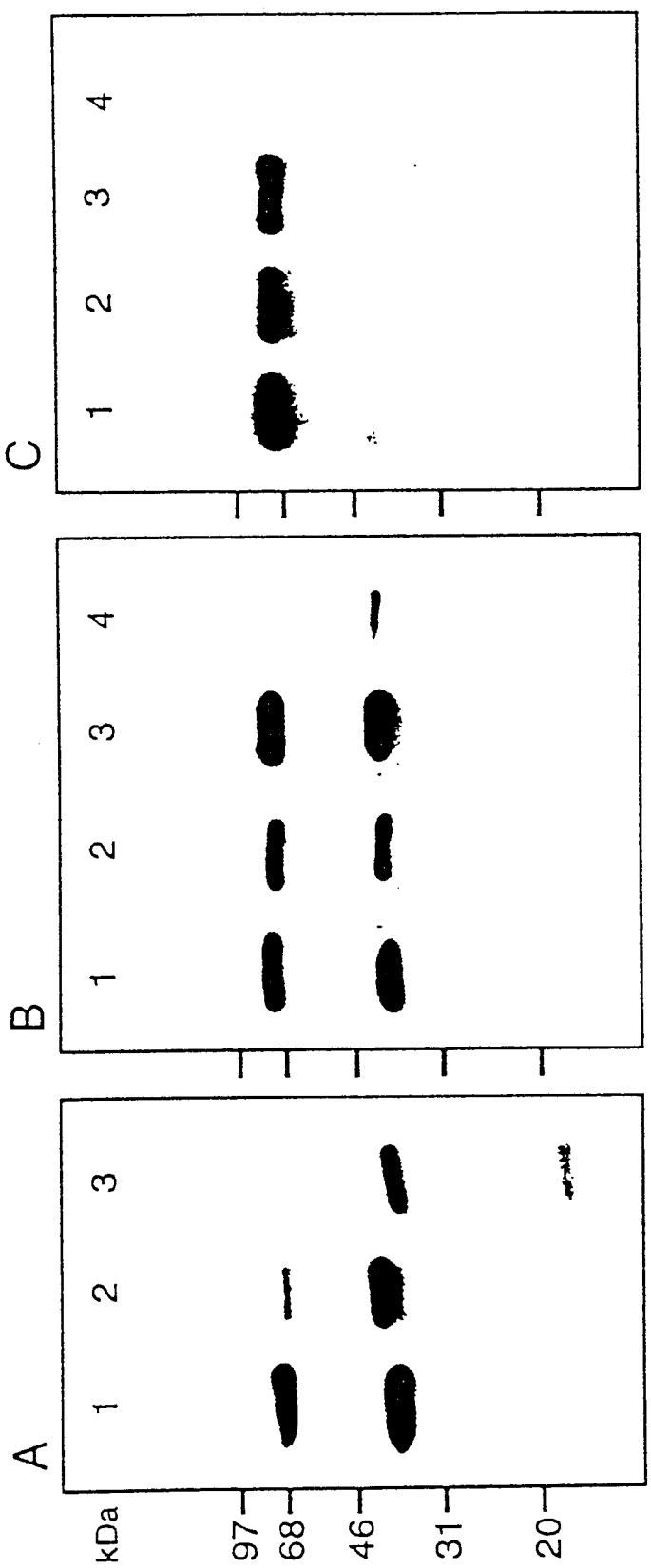
FIG. 3A–C shows the characterization of the molecular weight of the BabA adhesin by the use of receptor overlay analysis (FIG. 3A, B) and receptor activity directed affinity tagging of Bab A (FIG. 3C).

To clone the gene encoding BabA, the N-terminal 20 aa sequence was utilized for the construction of degenerate primers (18). Two sets of clones were identified which both encode two different but very similar proteins. Both genes code for proteins having almost identical N-terminal domains and identical C-terminal domains, complicating the identification of the functional BabA gene. (FIG. 5). To identify the corresponding gene, the BabA adhesin was purified in large scale by ReTagging. This provided enough protein for an extended amino terminal sequence. 41 amino acids were identified and these residues unambiguously discriminated between the two genes by the differences in aa-positions 28, 35, 37, 38 and 41 (FIG. 5). The gene encoding BabA was named babA and correspond to a basic protein with a pI of 9.4 and a molecular weight of 78 kDa, i.e. of slightly higher molecular weight than that predicted from the SDS PAGE analyses (FIG. 3). The other gene, babB, corresponds to a protein of a calculated molecular weight of 75.5 kDa. In contrast to babA, the babB gene contains a predicted translational initiation codon (FIG. 5). This could indicate the existence of a third bab gene in the genome or mechanisms for recombination activities. Interestingly, the bab-genes were also detected in strains lacking Lewis b binding properties (data not shown). Gene cassette systems have been shown to promote antigenic variation in *Neisseria gonorrhoeae* (19). Another possibility would be the presence of similar genes coding for adhesins with differences in receptor specificity/host tissue tropism (20). Gene inactivation experiments targeting the bab-genes could aid in understanding this complex gene organization.

Immunization experiments with adhesins from *Bordetella pertussis* (21) indicate the potential for outer membrane proteins to act as vaccine candidates (discussed in ref. 22).

In a mouse model for persistent *H. pylori* infection, oral immunization with *H. pylori* antigens proved protective against *H. pylori* infection (10). However, results from animal models are difficult to evaluate for human specific pathogens, such as *H. pylori* and Polio virus. For Polio, an animal model has been achieved by expressing the virus receptor in transgenic mice (23). A similar strategy was taken for *H. pylori*. A transgenic mouse was constructed by the use of an al,¾-fucosyltransferase, driving the synthesis of the human specific Le$^b$ antigen in the gastrointestinal tract (24). The Lewis b mouse can be useful for the evaluation of the role of the BabA adhesin as a colonization/virulence factor and in addition for the evaluation of BabA as a vaccine candidate against acid peptic disease and gastric adenocarcinoma.

In the present study the ReTagging technique was used for the purification of the adhesin part of the microbial receptor-ligand interaction. By the use of purified adhesin/lectin-protein, the ReTagging technique could, in addition, be used to further study the receptor part of the interaction. Identification of the biologically active receptor structure, carrying Le$^b$ oligosaccharides, would aid in the understanding of the mechanisms supporting the chronic *H. pylori* infection.

Although the invention has been described with regard to its preferred embodiments, which constitute, the best mode presently known to the inventors, it should be understood that various changes and modifications as would be obvious to one having the ordinary skill in this art may be made without departing from the scope of the invention which is set forth in the claims appended hereto.

REFERENCES AND NOTES

1. J. R. Warren, *Lancet*, i, 1273, 1983, B. Marshall, *Lancet*, i, 1273, 1983.
2. A. Dubois, *Emerging Infectious Diseases* 1, 79 (1995).
3. M. J. Blaser, *Sci. Amer.* 2, 92 (1996).
4. 3. M. J. Blaser, *Trends Microbiol.* 7, 255 (1993), D. E. Kirschner and M. J. Blaser, *J. Theor. Biol.* 176, 281 (1995).
5. P. Falk, T. Borén, and S. Normark, *Meth. Enzymol.* 236, 353 (1994).
6. D. G. Evans, D. J. Evans Jr., J. J. Moulds and D. Y. Graham, *Infect. Immun.* 56, 2896 (1988), S. Hirmo, M. Utt, M. Ringner and T. Wadström, *FEMS Immunol. and Med. Microbiol.* 10, 301 (1995), T. Saitoh, et al *FEBS Lett.* 282, 385 (1991).
7. T. Borén, P. Falk, K. A. Roth, G. Larson, and S. Normark, *Science.* 262, 1892 (1993), P. Falk, et al *Proc. Natl. Acad. Sci. U.S.A.* 90, 2035 (1993).
8. *H. pylori* strain CCUG 17875 was obtained from CCUG, Göteborg, Sweden. Strain A5, a gastric ulcer isolate, came from Astra Arcus, Södertädlje, Sweden. Strains P466 and MO19 were described previously (7). Strain 26695 came from Dr. K A. Eaton, The Ohio State University, and its genome was recently sequenced by The Institute for Genomic Research (TIGR), Rockville, Md. (J.-F. Tomb, et al, abstract 3B: 059, IX International Workshop on Gastroduodenal Pathology and *Helicobacter pylori*, Copenhagen, Denmark, 1996). The panel of 45 *H. pylori* clinical isolates came from the University Hospital in Uppsala, Sweden. Bacteria were grown at 37(C in 10% $CO_2$ and 5% $O_2$ for 48 h.
9. All blood group antigen glycoconjugates used, i.e. semisynthetic glycoproteins constructed by the conjugation of purified fucosylated oligosaccharides to serum albumin (7, 25), were from IsoSep AB, Tullinge, Sweden. The RIA was performed according to ref. 26 with some modifications; The H-1, Le$^b$, Le$^a$. H-2, Le$^x$, and Le$^Y$ glycoconjugates were $^{125}$I-labeled by the Chloramine T method. 1 mL of bacteria (A$_{600}$=OD 0.10) was incubated with 300 ng of $^{125}$I-labeled conjugate (i.e. an excess of receptors) for 30 min. in phosphate buffered saline (PBS), 0.5% albumin, 0.05% Tween-20 (BB-buffer). After centrifugation, $^{125}$I-activity in the bacterial pellet was measured by gamma scintillation counting.

10. A. Covacci, et al, *Proc. Natl. Acad. Sci. U.S.A.* 90, 5791 (1993), M. Marchetti, et al, *Science* 267, 1655 (1995).

11. S. Censini et al, *Proc. Natl. Acad. Sci. U.S.A.* 93, 14648, (1996).

12. Z. Xiang, et al, *Infect. Immun.* 63, 94 (1995).

13. A. G. Scatchard, *Ann. N. Y Acad. Sci.* 51, 600 (1949).

14. O. Mol, and B. Oudega, FEMS. *Microbiol. Reviews,* 19, 25 (1996).

15. Confocal microscopy was performed on a Nikon/Multiprobe 2001 instrument (Molecular Dynamics, Sunnyvale, Calif.). Electron microscopy was performed on a JEOL 100 CX instrument.

16. J. Brunner, *Trends in Cell Biol.* 6, 154 (1996), J. D. Bleil and P. M. Wassarman, *Proc. Natl. Acad. Sci. U.S.A.* 87, 5563, (1990).

17. M. M. Exner, P. Doig, T. J. Trust, and R. E. W. Hancock, *Infect. Immun.* 63, 1567 (1995), P. Doig, M. M. Exner, R. E. W. Hancock and T. J. Trust, *J. Bacteriol.* 177, 5447 (1995).

18. The BabA N-terminal sequence analysis was used to make degenerate oligonucleotides which were used in PCR to obtain an amplified fragment from the chromosome of the babA gene. A 59 bp fragment was identified and used as probe for the screening of a low-copy plasmid (pACYC184) library of Sau3A partially digested chromosomal DNA from strain CCUG 17875.

19. P. Hagblom, E. Segal, E. Billyard, and M. So, *Nature,* 315, 156 (1985), R. Haas and T. F. Meyer, *Cell,* 44, 107 (1986).

20. A.-B. Jonsson, D. Ilver, P. Falk, J. Pepose, and S. Normark, *Mol. Microbiol,* 13, 403 (1994), N. Strömberg, P. G. Nyholm, I. Pascher, and S. Normark, *Proc. Natl. Acad. Sci USA* 88, 9340 (1991).

21. A. Kimura, K. T. Mountzouros, D. A. Relman, S. Falkow, J. L. Cowell, *Infect. Immun.* 58, 7 (1990).

22. T. Borén, and P. Falk, *Sci. Amer., Sci. & Med.* 4 (1994), L. S. Tompkins and S. Falkow, *Science* 267, 1621 (1995).

23. R. B. Ren, et al, *Cell* 63, 353 (1990).

24. P. G. Falk, L. Bry, J. Holgersson, and J. I. Gordon, *Proc. Natl. Acad. Sci. U.S.A.* 92, 1515 (1995).

25. P. D. Rye, *Nature Biotechnology.* 2, 155 (1996).

26. P. Falk, T. Borén, D. Haslam, M. G. Caparon, *Meth. Cell Biol.* 45, 161 (1994)

27. Cell extracts were prepared in SDS sample buffer without mercaptoethanol and heated at 37° C. or 97° C. for 10 min. before separation on SDS-PAGE. Proteins were blotted onto a PVDF membrane. The membrane was incubated with 1 μg/mL biotinylated Le$^b$ glycoconjugate or biotinylated albumin (negative control) overnight, labeled as described in ref. 7. After washing in PBS/0.05% Tween-20, the biotinylated structures bound by the BabA band were probed by HRP-streptavidin and detected using ECL reagents (Amersham, Buckinghamshire, England).

28. The bacterial suspension was incubated with Le$^b$ glycoconjugate, to which the Sulfo-SBED crosslinker (Pierce, Rockville, Ill.) had been conjugated by the N-hydroxysuccinimide ester (NHS), according to the manufacturers specifications. The aryl azide crosslinker group was activated by UV irradiation (360 nm). Bacteria were washed with PBS pH 7.6, 0.05% Tween-20 and protease inhibitors (EDTA and benzamidine) under reducing conditions with 50 mM dithiothreitol (DTT). Bacterial proteins were separated on SDS-PAGE, and the biotin tagged BabA protein was detected by immunodetection (PVDF membrane/ HRP-streptavidin and ECL) (FIG. 3C).

29. Strains CCUG 17875 and A5 were first processed by crosslinking and DTT treatment, as above (28), followed by solubilization in SDS sample buffer. The biotin tagged BabA protein was then extracted with streptavidin coated magnetic beads (Advanced Magnetics Inc., Cambridge, Mass.). The beads were boiled in SDS sample buffer, and bound proteins were eluted and alkylated. The protein preparation was further fractionated by preparative SDS-PAGE (Prep-Cell 491, BioRad, Hercules, Calif.). Fractions with the biotin tagged protein, i.e. the BabA fractions, were identified by immunodetection using streptavidin/ECL. The pooled BabA preparation was then separated on SDS-PAGE and transferred to PVDF membrane. The BabA band was excised and the BabA protein was N-terminally sequenced using a Procise™ 494 instrument (Applied Biosystems, Foster City, Calif.).

What is claimed is:

1. An isolated recombinant DNA from *Helicobacter pylori* encoding an adhesin protein, wherein said protein specifically binds to the fucosylated blood group antigens Lewis[b] and H-1, comprising the nucleotide acid sequence of SEQ ID NO:1.

2. A vector comprising an isolated recombinant DNA from *Helicobacter pylori* encoding an adhesin protein, wherein said protein specifically binds to the fucosylated blood group antigens Lewis[b] and H-1, comprising the nucleotide sequence of SEQ ID NO:1.

3. An isolated recombinant DNA from *Helicobacter pylori* encoding an adhesion protein, wherein said protein specifically binds to the fucosylated blood group antigens Lewis[b] and H-1, comprising the open reading frame of the nucleotide sequence of SEQ ID NO:1.

4. A vector comprising an isolated recombinant DNA from Helicobacter pyroli encoding an adhesin protein, wherein said protein specifically binds to the fucosylated blood group antigens Lewis[b] and H-1, comprising the open reading frame of the nucleotide sequence of SEQ ID NO:1.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 3340 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS (B) LOCATION: 690..2924

(xi) SEQUENCE DESCRIPTION: SEQ ID NO:1:

```
TTTCAGTCAA GCCCAAAGCT ATGCGCAAAA CGCTTATGCT AAAGAGAATT TACAAGCACA    60

GCCGTCCAAG TATCAAAACA GCGTGCCTGA AATCAATATT GATGAAGAAG AAATCCCCTT   120

TAAGGGTTAA AATTAAGGAG ACATTATGGA AAGAAAACGC TATTCAAAAC GCTATTGCAA   180

ATACACTGAA GCTAAAATCA GCTTTATTGA CTATAAAGAT TTGGACATGC TCAAGCACAC   240

GCTATCAGAG CGCTATAAAA TCATGCCAAG GAGGTTGACA GGCAATAGCA AAAAGTGGCA   300

AGAGAGGGTG GAAGTTAGCG ATCAAAGAG  CCCGCCACAT GGCTTTAATC CCCTACATTG   360

TGGATAGGAA AAAAGTCGTG GATAGCCCTT TTAAACAGCA CTGAATTTTT GATTAGGGCT   420

AATAGGGGGC ATGCCTTTTA ATCTTGTTTA ATCTTGGCTC TATTTTTGTT AAACATCGGT   480

TATAAAAGCG TTAAAAGCAC TTTTAAAATC CAATTAAAAG CGTTCAAAAG TAACGCAAAA   540

AATCAAAAAA ATGACAAAAT TTTTAAGAAA ATGACAAAAA AAAAAAAAAC GCTTTATGCT   600

ATAATATTCC AAATACATTC TAATGCAAAT GCATTCTAAT GCAAATGTAT AATGAATGTA   660
```

```
TGAAATCCCT AATATTCAAT CCAATTTAA TCC AAA AAG GAG AAA AAA CAC ATC     713
                                 Ser Lys Lys Glu Lys Lys His Ile
                                  1               5

CTT TCA TTA ACT TTA GGC TCG CTT TTA GTT TCC ACT TTG AGC GCT GAA    761
Leu Ser Leu Thr Leu Gly Ser Leu Leu Val Ser Thr Leu Ser Ala Glu
         10              15                  20

GAC GAC GGC TTT TAC ACA AGC GTA GGC TAT CAA ATC GGT GAA GCC GCT    809
Asp Asp Gly Phe Tyr Thr Ser Val Gly Tyr Gln Ile Gly Glu Ala Ala
 25                  30                  35                  40

CAA ATG GTA ACA AAC ACC AAA GGC ATC CAA GAT CTT TCA GAC AAC TAT    857
Gln Met Val Thr Asn Thr Lys Gly Ile Gln Asp Leu Ser Asp Asn Tyr
                 45                  50                  55

GAA AAC TTG AGC AAA CTT TTG ACC CGA TAC AGC ACC CTA AAC ACC CTT    905
Glu Asn Leu Ser Lys Leu Leu Thr Arg Tyr Ser Thr Leu Asn Thr Leu
             60                  65                  70

ATC AAA TTG TCC GCT GAT CCG AGC GCG ATT AAC GCG GCA CGT GAA AAT    953
Ile Lys Leu Ser Ala Asp Pro Ser Ala Ile Asn Ala Ala Arg Glu Asn
         75                  80                  85

CTG GGC GCG AGC GCG AAG AAC TTG ATC GGC GAT ACC AAA AAT TCC CCC   1001
Leu Gly Ala Ser Ala Lys Asn Leu Ile Gly Asp Thr Lys Asn Ser Pro
     90                  95                 100

GCC TAT CAA GCC GTG CTT TTG GCG ATC AAT GCG GCG GTA GGG TTT TGG   1049
Ala Tyr Gln Ala Val Leu Leu Ala Ile Asn Ala Ala Val Gly Phe Trp
105                 110                 115                 120

AAT GTC TTA GGC TAT GCT ACG CAA TGC GGG GGT AAC GCT AAT GGT CAA   1097
Asn Val Leu Gly Tyr Ala Thr Gln Cys Gly Gly Asn Ala Asn Gly Gln
                125                 130                 135

GAA AGC ACC TCT TCA ACC ACC ATC TTC AAC AAC GAG CCA GGG TAT CGA   1145
Glu Ser Thr Ser Ser Thr Thr Ile Phe Asn Asn Glu Pro Gly Tyr Arg
            140                 145                 150

TCC ACT TCC ATC ACT TGC AGT TTG AAC AGG TAT AAG CCT GGA TAC TAC   1193
Ser Thr Ser Ile Thr Cys Ser Leu Asn Arg Tyr Lys Pro Gly Tyr Tyr
        155                 160                 165

GGC CCT ATG AGC ATT GAA AAT TTC AAA AAG CTT AAC GAA GCC TAT CAA   1241
Gly Pro Met Ser Ile Glu Asn Phe Lys Lys Leu Asn Glu Ala Tyr Gln
    170                 175                 180

ATC CTC CAA ACG GCT TTA AAT AAA GGC TTA CCC GCG CTC AAA GAA AAC   1289
Ile Leu Gln Thr Ala Leu Asn Lys Gly Leu Pro Ala Leu Lys Glu Asn
185                 190                 195                 200

AAC GGA ACG GTC AGT GTA ACC TAC ACC TAC ACA TGC TCA GGG GAA GGG   1337
```

```
                                                              -continued

Asn Gly Thr Val Ser Val Thr Tyr Thr Tyr Thr Cys Ser Gly Glu Gly
            205                 210                 215

AAT GAT AAC TGC TCG AAA AAA GCC ACA GGT GTA AGT GAC CAA AAT GGC      1385
Asn Asp Asn Cys Ser Lys Lys Ala Thr Gly Val Ser Asp Gln Asn Gly
            220                 225                 230

GGA ACC AAA ACT AAA ACC CAA ACC ATA GAC GGC AAA ACC GTA ACC ACC      1433
Gly Thr Lys Thr Lys Thr Gln Thr Ile Asp Gly Lys Thr Val Thr Thr
            235                 240                 245

ACG ATC AGT TCA AAA GTC GTT GAT AGT CAG GCA AAA GGT AAT ACA ACA      1481
Thr Ile Ser Ser Lys Val Val Asp Ser Gln Ala Lys Gly Asn Thr Thr
            250                 255                 260

AGG GTG TCC TAC ACC GAA ATC ACT AAC AAA TTA GAC GGT GTG CCT GAT      1529
Arg Val Ser Tyr Thr Glu Ile Thr Asn Lys Leu Asp Gly Val Pro Asp
265                 270                 275                 280

AGC GCT CAA GCG CTC TTG GCA CAA GCG AGC ACG CTC ATC AAC ACC ATC      1577
Ser Ala Gln Ala Leu Leu Ala Gln Ala Ser Thr Leu Ile Asn Thr Ile
            285                 290                 295

AAC ACG GCA TGC CCG TAT TTT AGT GTA ACT AAT AAA AGT GGT GGT CCA      1625
Asn Thr Ala Cys Pro Tyr Phe Ser Val Thr Asn Lys Ser Gly Gly Pro
            300                 305                 310

CAG ATG GAA CCG ACT AGA GGG AAG TTG TGC GGT TTT ACA GAA GAA ATC      1673
Gln Met Glu Pro Thr Arg Gly Lys Leu Cys Gly Phe Thr Glu Glu Ile
            315                 320                 325

AGC GCG ATC CAA AAG ATG ATC ACA GAC GCG CAA GAG CTG GTC AAT CAA      1721
Ser Ala Ile Gln Lys Met Ile Thr Asp Ala Gln Glu Leu Val Asn Gln
            330                 335                 340

ACG AGC GTC ATT AAC GAG CAT GAA CAA TCA ACC CCG GTA GGC GGT AAT      1769
Thr Ser Val Ile Asn Glu His Glu Gln Ser Thr Pro Val Gly Gly Asn
345                 350                 355                 360

AAT GGC AAG CCT TTC AAC CCT TTC ACG GAC GCA AGC TTC GCT CAA GGC      1817
Asn Gly Lys Pro Phe Asn Pro Phe Thr Asp Ala Ser Phe Ala Gln Gly
            365                 370                 375

ATG CTC GCT AAC GCT AGT GCG CAA GCC AAA ATG CTC AAT CTA GCC CAT      1865
Met Leu Ala Asn Ala Ser Ala Gln Ala Lys Met Leu Asn Leu Ala His
            380                 385                 390

CAA GTG GGG CAA ACC ATT AAC CCT GAC AAT CTT ACC GGG ACT TTT AAA      1913
Gln Val Gly Gln Thr Ile Asn Pro Asp Asn Leu Thr Gly Thr Phe Lys
            395                 400                 405

AAT TTT GTT ACA GGC TTT TTA GCC ACA TGC AAC AAC AAA TCA ACA GCT      1961
Asn Phe Val Thr Gly Phe Leu Ala Thr Cys Asn Asn Lys Ser Thr Ala
            410                 415                 420

GGC ACT AGT GGC ACA CAA GGT TCA CCT CCT GGC ACA GTA ACC ACT CAA      2009
Gly Thr Ser Gly Thr Gln Gly Ser Pro Pro Gly Thr Val Thr Thr Gln
425                 430                 435                 440

ACT TTC GCT TCC GGT TGC GCC TAT GTG GAG CAA ACC ATA ACG AAT CTA      2057
Thr Phe Ala Ser Gly Cys Ala Tyr Val Glu Gln Thr Ile Thr Asn Leu
            445                 450                 455

AAC AAC AGC ATC GCT CAT TTT GGC ACT CAA GAG CAG CAG ATA CAG CAA      2105
Asn Asn Ser Ile Ala His Phe Gly Thr Gln Glu Gln Gln Ile Gln Gln
            460                 465                 470

GCT GAA AAC ATC GCT GAC ACT CTA GTG AAT TTC AAA TCT AGA TAC AGC      2153
Ala Glu Asn Ile Ala Asp Thr Leu Val Asn Phe Lys Ser Arg Tyr Ser
            475                 480                 485

GAA TTA GGG AAT ACT TAT AAC AGC ATC ACT ACT GCG CTC TCC AAA GTC      2201
Glu Leu Gly Asn Thr Tyr Asn Ser Ile Thr Thr Ala Leu Ser Lys Val
            490                 495                 500

CCT AAC GCG CAA AGC TTG CAA AAC GTG GTG GGA AAA AAG AAT AAC CCC      2249
Pro Asn Ala Gln Ser Leu Gln Asn Val Val Gly Lys Lys Asn Asn Pro
505                 510                 515                 520
```

```
TAT AGC CCG CAA GGC ATA GAA ACC AAT TAC TAC TTG AAT CAA AAC TCT    2297
Tyr Ser Pro Gln Gly Ile Glu Thr Asn Tyr Tyr Leu Asn Gln Asn Ser
                525                 530                 535

TAC AAC CAA ATC CAA ACC ATC AAC CAA GAA TTA GGG CGT AAC CCC TTT    2345
Tyr Asn Gln Ile Gln Thr Ile Asn Gln Glu Leu Gly Arg Asn Pro Phe
                540                 545                 550

AGG AAA GTG GGC ATC GTC AGT TCT CAA ACC AAC AAT GGT GCC ATG AAT    2393
Arg Lys Val Gly Ile Val Ser Ser Gln Thr Asn Asn Gly Ala Met Asn
                555                 560                 565

GGG ATC GGT ATC CAG GTG GGC TAC AAG CAA TTC TTT GGG CAA AAA AGG    2441
Gly Ile Gly Ile Gln Val Gly Tyr Lys Gln Phe Phe Gly Gln Lys Arg
                570                 575                 580

AAA TGG GGT GCA AGA TAC TAC GGC TTT TTT GAT TAC AAC CAT GCG TTC    2489
Lys Trp Gly Ala Arg Tyr Tyr Gly Phe Phe Asp Tyr Asn His Ala Phe
585                 590                 595                 600

ATT AAA TCC AGC TTC TTC AAC TCG GCT TCT GAC GTG TGG ACT TAT GGT    2537
Ile Lys Ser Ser Phe Phe Asn Ser Ala Ser Asp Val Trp Thr Tyr Gly
                605                 610                 615

TTT GGA GCG GAC GCT CTT TAT AAC TTC ATC AAC GAT AAA GCC ACC AAT    2585
Phe Gly Ala Asp Ala Leu Tyr Asn Phe Ile Asn Asp Lys Ala Thr Asn
                620                 625                 630

TTC TTA GGC AAA AAC AAC AAG CTT TCT GTG GGG CTT TTT GGC GGG ATT    2633
Phe Leu Gly Lys Asn Asn Lys Leu Ser Val Gly Leu Phe Gly Gly Ile
                635                 640                 645

GCG TTA GCG GGC ACT TCA TGG CTT AAT TCT GAA TAC GTG AAT TTA GCC    2681
Ala Leu Ala Gly Thr Ser Trp Leu Asn Ser Glu Tyr Val Asn Leu Ala
650                 655                 660

ACC ATG AAT AAC GTC TAT AAC GCT AAA ATG AAC GTG GCG AAC TTC CAA    2729
Thr Met Asn Asn Val Tyr Asn Ala Lys Met Asn Val Ala Asn Phe Gln
665                 670                 675                 680

TTC TTA TTC AAC ATG GGA GTG AGG ATG AAT TTA GCC AGA TCC AAG AAA    2777
Phe Leu Phe Asn Met Gly Val Arg Met Asn Leu Ala Arg Ser Lys Lys
                685                 690                 695

AAA GGC AGC GAT CAT GCG GCT CAG CAT GGC ATT GAG TTA GGG CTT AAA    2825
Lys Gly Ser Asp His Ala Ala Gln His Gly Ile Glu Leu Gly Leu Lys
                700                 705                 710

ATC CCC ACC ATT AAC ACG AAC TAC TAT TCC TTT ATG GGG GCT GAA CTC    2873
Ile Pro Thr Ile Asn Thr Asn Tyr Tyr Ser Phe Met Gly Ala Glu Leu
                715                 720                 725

AAA TAC CGC AGG CTC TAT AGC GTG TAT TTG AAT TAT GTG TTC GCT TAC    2921
Lys Tyr Arg Arg Leu Tyr Ser Val Tyr Leu Asn Tyr Val Phe Ala Tyr
                730                 735                 740

TAA AAACTAAAAA TCCTTTGTGG AACTCCCTTT TTAAGGGGTT TCTTTTAAAG          2974
 *
745

CCTTTATTTT TTTTTGGAGG GGTTTAATTT TTTTGAAACC TTTGTTTTTG AATTCTCTTT   3034

TTAATGGGTT TCTTTTTTGA ACTCTTTGTT TTGAACTCCT TTTTTTGAAC TCCCTTTTTT   3094

AAACCCTTTC TTTTTTAAAA TTCTCTTTTT TGGGGGGTTT GATGAAAAAT CCTTTTTTAG   3154

CGTTTTGGTA TTGGTTAGTG GAAAACTTGA TACTAATTTA AGCGATAGTT TTTAAAAAGT   3214

GCTTCTTTAA TATAGGGGGT TTAAGTTGGT GATTAAAAGG GGGGAATGGT TTCAAAGCGC   3274

TTCCTATCCC TTTAAGAAAA TAAAATAAAA CTTTAATAAA ATGAGTTTTA CAACAAAATG   3334

AGATCC                                                             3340

(2) INFORMATION FOR SEQ ID NO:2:

(i) SEQUENCE CHARACTERISTICS:
        (A) LENGTH: 744 amino acids
```

(B) TYPE: amino acid
    (D) TOPOLOGY: linear (ii) MOLECULE TYPE: protein (xi) SEQUENCE DESCRIPTION: SEQ ID NO:2:

```
Ser Lys Lys Glu Lys Lys His Ile Leu Ser Leu Thr Leu Gly Ser Leu
 1               5                   10                  15

Leu Val Ser Thr Leu Ser Ala Glu Asp Asp Gly Phe Tyr Thr Ser Val
                20                  25                  30

Gly Tyr Gln Ile Gly Glu Ala Ala Gln Met Val Thr Asn Thr Lys Gly
            35                  40                  45

Ile Gln Asp Leu Ser Asp Asn Tyr Glu Asn Leu Ser Lys Leu Leu Thr
        50                  55                  60

Arg Tyr Ser Thr Leu Asn Thr Leu Ile Lys Leu Ser Ala Asp Pro Ser
 65                  70                  75                  80

Ala Ile Asn Ala Ala Arg Glu Asn Leu Gly Ala Ser Ala Lys Asn Leu
                85                  90                  95

Ile Gly Asp Thr Lys Asn Ser Pro Ala Tyr Gln Ala Val Leu Leu Ala
            100                 105                 110

Ile Asn Ala Ala Val Gly Phe Trp Asn Val Leu Gly Tyr Ala Thr Gln
        115                 120                 125

Cys Gly Gly Asn Ala Asn Gly Gln Glu Ser Thr Ser Ser Thr Thr Ile
    130                 135                 140

Phe Asn Asn Glu Pro Gly Tyr Arg Ser Thr Ser Ile Thr Cys Ser Leu
145                 150                 155                 160

Asn Arg Tyr Lys Pro Gly Tyr Tyr Gly Pro Met Ser Ile Glu Asn Phe
                165                 170                 175

Lys Lys Leu Asn Glu Ala Tyr Gln Ile Leu Gln Thr Ala Leu Asn Lys
            180                 185                 190

Gly Leu Pro Ala Leu Lys Glu Asn Gly Thr Val Ser Val Thr Tyr
        195                 200                 205

Thr Tyr Thr Cys Ser Gly Glu Gly Asn Asp Asn Cys Ser Lys Lys Ala
    210                 215                 220

Thr Gly Val Ser Asp Gln Asn Gly Gly Thr Lys Thr Lys Thr Gln Thr
225                 230                 235                 240

Ile Asp Gly Lys Thr Val Thr Thr Ile Ser Ser Lys Val Val Asp
                245                 250                 255

Ser Gln Ala Lys Gly Asn Thr Thr Arg Val Ser Tyr Thr Glu Ile Thr
            260                 265                 270

Asn Lys Leu Asp Gly Val Pro Asp Ser Ala Gln Ala Leu Leu Ala Gln
        275                 280                 285

Ala Ser Thr Leu Ile Asn Thr Ile Asn Thr Ala Cys Pro Tyr Phe Ser
    290                 295                 300

Val Thr Asn Lys Ser Gly Gly Pro Gln Met Glu Pro Thr Arg Gly Lys
305                 310                 315                 320

Leu Cys Gly Phe Thr Glu Glu Ile Ser Ala Ile Gln Lys Met Ile Thr
                325                 330                 335

Asp Ala Gln Glu Leu Val Asn Gln Thr Ser Val Ile Asn Glu His Glu
            340                 345                 350

Gln Ser Thr Pro Val Gly Gly Asn Asn Gly Lys Pro Phe Asn Pro Phe
        355                 360                 365

Thr Asp Ala Ser Phe Ala Gln Gly Met Leu Ala Asn Ala Ser Ala Gln
    370                 375                 380
```

```
Ala Lys Met Leu Asn Leu Ala His Gln Val Gly Gln Thr Ile Asn Pro
385                 390                 395                 400

Asp Asn Leu Thr Gly Thr Phe Lys Asn Phe Val Thr Gly Phe Leu Ala
            405                 410                 415

Thr Cys Asn Asn Lys Ser Thr Ala Gly Thr Ser Gly Thr Gln Gly Ser
            420                 425                 430

Pro Pro Gly Thr Val Thr Thr Gln Thr Phe Ala Ser Gly Cys Ala Tyr
            435                 440                 445

Val Glu Gln Thr Ile Thr Asn Leu Asn Ser Ile Ala His Phe Gly
    450                 455                 460

Thr Gln Glu Gln Gln Ile Gln Gln Ala Glu Asn Ile Ala Asp Thr Leu
465                 470                 475                 480

Val Asn Phe Lys Ser Arg Tyr Ser Glu Leu Gly Asn Thr Tyr Asn Ser
            485                 490                 495

Ile Thr Thr Ala Leu Ser Lys Val Pro Asn Ala Gln Ser Leu Gln Asn
            500                 505                 510

Val Val Gly Lys Lys Asn Asn Pro Tyr Ser Pro Gln Gly Ile Glu Thr
            515                 520                 525

Asn Tyr Tyr Leu Asn Gln Asn Ser Tyr Asn Gln Ile Gln Thr Ile Asn
    530                 535                 540

Gln Glu Leu Gly Arg Asn Pro Phe Arg Lys Val Gly Ile Val Ser Ser
545                 550                 555                 560

Gln Thr Asn Asn Gly Ala Met Asn Gly Ile Gly Ile Gln Val Gly Tyr
            565                 570                 575

Lys Gln Phe Phe Gly Gln Lys Arg Lys Trp Gly Ala Arg Tyr Tyr Gly
            580                 585                 590

Phe Phe Asp Tyr Asn His Ala Phe Ile Lys Ser Ser Phe Asn Ser
    595                 600                 605

Ala Ser Asp Val Trp Thr Tyr Gly Phe Gly Ala Asp Ala Leu Tyr Asn
    610                 615                 620

Phe Ile Asn Asp Lys Ala Thr Asn Phe Leu Gly Lys Asn Asn Lys Leu
625                 630                 635                 640

Ser Val Gly Leu Phe Gly Gly Ile Ala Leu Ala Gly Thr Ser Trp Leu
            645                 650                 655

Asn Ser Glu Tyr Val Asn Leu Ala Thr Met Asn Asn Val Tyr Asn Ala
            660                 665                 670

Lys Met Asn Val Ala Asn Phe Gln Phe Leu Phe Asn Met Gly Val Arg
    675                 680                 685

Met Asn Leu Ala Arg Ser Lys Lys Gly Ser Asp His Ala Ala Gln
    690                 695                 700

His Gly Ile Glu Leu Gly Leu Lys Ile Pro Thr Ile Asn Thr Asn Tyr
705                 710                 715                 720

Tyr Ser Phe Met Gly Ala Glu Leu Lys Tyr Arg Arg Leu Tyr Ser Val
            725                 730                 735

Tyr Leu Asn Tyr Val Phe Ala Tyr
            740                 745

(2) INFORMATION FOR SEQ ID NO:3:

(i) SEQUENCE CHARACTERISTICS:
        (A) LENGTH: 2781 base pairs
        (B) TYPE: nucleic acid
        (C) STRANDEDNESS: double
        (D) TOPOLOGY: linear (ii) MOLECULE TYPE: DNA (genomic)
```

-continued (ix) FEATURE:
    (A) NAME/KEY: CDS
    (B) LOCATION: 409..2532

(xi) SEQUENCE DESCRIPTION: SEQ ID NO:3:

```
CATTTGATCG CATTGGATTT CAAAGAAGGG CGTTTTGTGA AAGGCTTTGG TCAAGCTTAT      60

GATATTTTAG GCGACAAAAT CGCTTATGTT GGGGGTAAAG GCAACCCACA CAATTTCGCT     120

CACAAGAAAT AAACTTTCTC ACCCATAAGG GGCAAACGCC CCCAAAAGAG TGCTTTTTAA     180

AGAGGTTAAG GCAAAATCAA GCTCTTTAGT ATTTAATCTT AAAAAATACT AAAAGCCTTT     240

TTATGGGCTA ACACCACACA AAAAGCGTCA AAATCAAAAA AATGACAAAA TTTTCCCCAA     300

ATGACAAAAA AAAAAAAAAA CGATTTTATG CTATATTAAC GAAATCTTGT GATAAGATCT     360

TATTCTTTTA AAAGATTTAC CTAACCATTT TAATTTCAAG GAGAAAAC ATG AAA AAA      417
                                                    Met Lys Lys

AAC CCT TTT ACT CTC TCT CTC TCT CTC TCG TTT TTG CTC CAC GCT GAA      465
Asn Pro Phe Thr Leu Ser Leu Ser Leu Ser Phe Leu Leu His Ala Glu
    750             755             760

GAC GAC GGC TTT TAC ACA AGC GTA GGC TAT CAA ATC GGT GAA GCC GCT      513
Asp Asp Gly Phe Tyr Thr Ser Val Gly Tyr Gln Ile Gly Glu Ala Ala
765             770             775             780

CAA ATG GTA ACC AAC ACC AAA GGC ATC CAA CAG CTT TCA GAC AAT TAT      561
Gln Met Val Thr Asn Thr Lys Gly Ile Gln Gln Leu Ser Asp Asn Tyr
                785             790             795

GAA AAG CTG AAC AAT CTT TTG AAT AAT TAC AGC ACC CTA AAC ACC CTT      609
Glu Lys Leu Asn Asn Leu Leu Asn Asn Tyr Ser Thr Leu Asn Thr Leu
            800             805             810

ATC AAA TTA TCC GCT GAT CCG AGT GCG ATT AAC GAC GCA AGG GAT AAT      657
Ile Lys Leu Ser Ala Asp Pro Ser Ala Ile Asn Asp Ala Arg Asp Asn
        815             820             825

CTA GGC TCA AGT GCT AAG AAT TTG CTT GAT GTT AAA ACC AAC TCC CCG      705
Leu Gly Ser Ser Ala Lys Asn Leu Leu Asp Val Lys Thr Asn Ser Pro
    830             835             840

GCC TAT CAA GCC GTG CTT TTA GCG TTG AAT GCG GCG GTG GGG TTG TGG      753
Ala Tyr Gln Ala Val Leu Leu Ala Leu Asn Ala Ala Val Gly Leu Trp
845             850             855             860

CAA GTT ACA AGC TAC GCT TTT ACT GCT TGT GGT CCT GGC AGT AAC GAG      801
Gln Val Thr Ser Tyr Ala Phe Thr Ala Cys Gly Pro Gly Ser Asn Glu
                865             870             875

AGC GCA AAT GGA GGT ATC CAA ACT TTT AAT AAT GTG CCA GGA CAA AAG      849
Ser Ala Asn Gly Gly Ile Gln Thr Phe Asn Asn Val Pro Gly Gln Lys
            880             885             890

ACG ACA ACC ATC ACT TGC AAT TCG TAT TAT CAA CCA GGA CAT GGT GGG      897
Thr Thr Thr Ile Thr Cys Asn Ser Tyr Tyr Gln Pro Gly His Gly Gly
        895             900             905

CCT ATA TCC ACT GCA AAC TAT GCA AAA ATC AAT CAA GCC TAT CAA ATC      945
Pro Ile Ser Thr Ala Asn Tyr Ala Lys Ile Asn Gln Ala Tyr Gln Ile
    910             915             920

ATT CAA AAG GCT TTG ACA GCC AAT GAA GCT AAT GGA GAT GGG GTC CCC      993
Ile Gln Lys Ala Leu Thr Ala Asn Glu Ala Asn Gly Asp Gly Val Pro
925             930             935             940

GTT TTA AGC GAC ACC ACT ACA AAA CTT GAT TTC ACT ATT CAA GGA GAC     1041
Val Leu Ser Asp Thr Thr Thr Lys Leu Asp Phe Thr Ile Gln Gly Asp
                945             950             955

AAA AGA ACG GGT GGC CGA CCA AAT ACA CCT AAA AAG TTC CCA TGG AGT     1089
Lys Arg Thr Gly Gly Arg Pro Asn Thr Pro Lys Lys Phe Pro Trp Ser
            960             965             970

GAT GGG AAA TAT ATT CAC ACC CAA TGG ATT GAC ACA ACA CCA CAA TCA     1137
```

-continued

```
Asp Gly Lys Tyr Ile His Thr Gln Trp Ile Asp Thr Thr Pro Gln Ser
        975                 980                 985

ACA GAA ACA AAG ATC AAC ACA GAA AAT AAC GCT CAA GAG CTT TTA AAA      1185
Thr Glu Thr Lys Ile Asn Thr Glu Asn Asn Ala Gln Glu Leu Leu Lys
        990                 995                 1000

CAA GCG AGC ATC ATT ATC ACT ACC CTA AAT GAG GCA TGC CCA AAC TTC      1233
Gln Ala Ser Ile Ile Ile Thr Thr Leu Asn Glu Ala Cys Pro Asn Phe
1005                1010                1015                1020

CAA AAT GGT GGT AGC GGT TAT TGG CAA GGG ATA AGC GGC AAT GGG ACA      1281
Gln Asn Gly Gly Ser Gly Tyr Trp Gln Gly Ile Ser Gly Asn Gly Thr
            1025                1030                1035

ATG TGT GGG ATG TTT AAG AAT GAA ATC AGC GCT ATC CAA GGC ATG ATC      1329
Met Cys Gly Met Phe Lys Asn Glu Ile Ser Ala Ile Gln Gly Met Ile
                1040                1045                1050

GCT AAC GCG CAA GAA GCT GTC GCG CAA AGT AAA ATC GTT AGT GAA AAT      1377
Ala Asn Ala Gln Glu Ala Val Ala Gln Ser Lys Ile Val Ser Glu Asn
            1055                1060                1065

GCG CAA AAT CAA AAC AAC TTG GAT ACT GGA AAA CCA TTC AAC CCT TTC      1425
Ala Gln Asn Gln Asn Asn Leu Asp Thr Gly Lys Pro Phe Asn Pro Phe
        1070                1075                1080

ACG GAC GCT AGC TTC GCT CAA AGC ATG CTC AAA AAC GCT CAA GCC CAA      1473
Thr Asp Ala Ser Phe Ala Gln Ser Met Leu Lys Asn Ala Gln Ala Gln
1085                1090                1095                1100

GCA GAG ATT TTA AAC CAA GCC GAA CAA GTG GTG AAA AAC TTT GAA AAA      1521
Ala Glu Ile Leu Asn Gln Ala Glu Gln Val Val Lys Asn Phe Glu Lys
            1105                1110                1115

ATC CCT AAA AAT TTT GTA TCA GAC TCT TTA GGG GTG TGT TAT GAA GAG      1569
Ile Pro Lys Asn Phe Val Ser Asp Ser Leu Gly Val Cys Tyr Glu Glu
        1120                1125                1130

CAA GGG GGT GAG CGT AGG GGC ACC AAT CCA GGT CAG GTT ACT TCT AAC      1617
Gln Gly Gly Glu Arg Arg Gly Thr Asn Pro Gly Gln Val Thr Ser Asn
    1135                1140                1145

ACT TTC GCT TCC GGT TGC GCC TAT GTG GAG CAA ACC ATA ACG AAT CTA      1665
Thr Phe Ala Ser Gly Cys Ala Tyr Val Glu Gln Thr Ile Thr Asn Leu
        1150                1155                1160

AAC AAC AGC ATC GCT CAT TTT GGC ACT CAA GAG CAG CAG ATA CAG CAA      1713
Asn Asn Ser Ile Ala His Phe Gly Thr Gln Glu Gln Gln Ile Gln Gln
1165                1170                1175                1180

GCT GAA AAC ATC GCT GAC ACT CTA GTG AAT TTC AAA TCT AGA TAC AGC      1761
Ala Glu Asn Ile Ala Asp Thr Leu Val Asn Phe Lys Ser Arg Tyr Ser
            1185                1190                1195

GAA TTA GGG AAT ACT TAT AAC AGC ATC ACT ACT GCG CTC TCC AAA GTC      1809
Glu Leu Gly Asn Thr Tyr Asn Ser Ile Thr Thr Ala Leu Ser Lys Val
        1200                1205                1210

CCT AAC GCG CAA AGC TTG CAA AAC GTG GTG GGA AAA AAG AAT AAC CCC      1857
Pro Asn Ala Gln Ser Leu Gln Asn Val Val Gly Lys Lys Asn Asn Pro
    1215                1220                1225

TAT AGC CCG CAA GGC ATA GAA ACC AAT TAC TAC TTG AAT CAA AAC TCT      1905
Tyr Ser Pro Gln Gly Ile Glu Thr Asn Tyr Tyr Leu Asn Gln Asn Ser
        1230                1235                1240

TAC AAC CAA ATC CAA ACC ATC AAC CAA GAA TTA GGG CGT AAC CCC TTT      1953
Tyr Asn Gln Ile Gln Thr Ile Asn Gln Glu Leu Gly Arg Asn Pro Phe
1245                1250                1255                1260

AGG AAA GTG GGC ATC GTC AGT TCT CAA ACC AAC AAT GGT GCC ATG AAT      2001
Arg Lys Val Gly Ile Val Ser Ser Gln Thr Asn Asn Gly Ala Met Asn
            1265                1270                1275

GGG ATC GGT ATC CAG GTG GGC TAC AAG CAA TTC TTT GGG CAA AAA AGG      2049
Gly Ile Gly Ile Gln Val Gly Tyr Lys Gln Phe Phe Gly Gln Lys Arg
        1280                1285                1290
```

```
AAA TGG GGT GCA AGA TAC TAC GGC TTT TTT GAT TAC AAC CAT GCG TTC     2097
Lys Trp Gly Ala Arg Tyr Tyr Gly Phe Phe Asp Tyr Asn His Ala Phe
        1295                1300                1305

ATT AAA TCC AGC TTC TTC AAC TCG GCT TCT GAC GTG TGG ACT TAT GGT     2145
Ile Lys Ser Ser Phe Phe Asn Ser Ala Ser Asp Val Trp Thr Tyr Gly
    1310                1315                1320

TTT GGA GCG GAC GCT CTT TAT AAC TTC ATC AAC GAT AAA GCC ACC AAT     2193
Phe Gly Ala Asp Ala Leu Tyr Asn Phe Ile Asn Asp Lys Ala Thr Asn
1325                1330                1335                1340

TTC TTA GGC AAA AAC AAC AAG CTT TCT GTG GGG CTT TTT GGC GGG ATT     2241
Phe Leu Gly Lys Asn Asn Lys Leu Ser Val Gly Leu Phe Gly Gly Ile
            1345                1350                1355

GCG TTA GCG GGC ACT TCA TGG CTT AAT TCT GAA TAC GTG AAT TTA GCC     2289
Ala Leu Ala Gly Thr Ser Trp Leu Asn Ser Glu Tyr Val Asn Leu Ala
        1360                1365                1370

ACC ATG AAT AAC GTC TAT AAC GCT AAA ATG AAC GTG GCG AAC TTC CAA     2337
Thr Met Asn Asn Val Tyr Asn Ala Lys Met Asn Val Ala Asn Phe Gln
    1375                1380                1385

TTC TTA TTC AAC ATG GGA GTG AGG ATG AAT TTA GCC AGA TCC AAG AAA     2385
Phe Leu Phe Asn Met Gly Val Arg Met Asn Leu Ala Arg Ser Lys Lys
1390                1395                1400

AAA GGC AGC GAT CAT GCG GCT CAG CAT GGC ATT GAG TTA GGG CTT AAA     2433
Lys Gly Ser Asp His Ala Ala Gln His Gly Ile Glu Leu Gly Leu Lys
1405                1410                1415                1420

ATC CCC ACC ATT AAC ACG AAC TAC TAT TCC TTT ATG GGG GCT GAA CTC     2481
Ile Pro Thr Ile Asn Thr Asn Tyr Tyr Ser Phe Met Gly Ala Glu Leu
            1425                1430                1435

AAA TAC CGC AGG CTC TAT AGC GTG TAT TTG AAT TAT GTG TTC GCT TAC     2529
Lys Tyr Arg Arg Leu Tyr Ser Val Tyr Leu Asn Tyr Val Phe Ala Tyr
        1440                1445                1450

TAG AAACTAAAAA TCCTTTGTGG AACTCCCTTT TTAAGGGGTT TCTTTTAAAG          2582
  *

CCTTTATTTT TTTTTGGAGG GGTTTAATTT TTTTGAAACC TTTGTTTTTG AATTCTCTTT   2642

TTAATGGGTT TCTTTTTTGA ACTCTTTGTT TTGAACTCCT TTTTTTGAAC TCCCTTTTTT   2702

AAACCCTTTC TTTTTTAAAA TTCTCTTTTT TGGGGGGTTT GATGAAAAAT CCTTTTTTAG   2762

CGTTTTGGTA TTGGTTAGT                                                2781

(2) INFORMATION FOR SEQ ID NO:4:

(i) SEQUENCE CHARACTERISTICS:
         (A) LENGTH: 707 amino acids
         (B) TYPE: amino acid
         (D) TOPOLOGY: linear (ii) MOLECULE TYPE: protein (xi) SEQUENCE DESCRIPTION: SEQ ID NO:4:

Met Lys Lys Asn Pro Phe Thr Leu Ser Leu Ser Leu Ser Phe Leu Leu
  1               5                  10                  15

His Ala Glu Asp Asp Gly Phe Tyr Thr Ser Val Gly Tyr Gln Ile Gly
              20                  25                  30

Glu Ala Ala Gln Met Val Thr Asn Thr Lys Gly Ile Gln Gln Leu Ser
         35                  40                  45

Asp Asn Tyr Glu Lys Leu Asn Asn Leu Leu Asn Asn Tyr Ser Thr Leu
     50                  55                  60

Asn Thr Leu Ile Lys Leu Ser Ala Asp Pro Ser Ala Ile Asn Asp Ala
 65                  70                  75                  80

Arg Asp Asn Leu Gly Ser Ser Ala Lys Asn Leu Leu Asp Val Lys Thr
```

```
                    85                      90                      95
Asn Ser Pro Ala Tyr Gln Ala Val Leu Leu Ala Leu Asn Ala Ala Val
                100                 105                 110
Gly Leu Trp Gln Val Thr Ser Tyr Ala Phe Thr Ala Cys Gly Pro Gly
            115                 120                 125
Ser Asn Glu Ser Ala Asn Gly Gly Ile Gln Thr Phe Asn Asn Val Pro
        130                 135                 140
Gly Gln Lys Thr Thr Thr Ile Thr Cys Asn Ser Tyr Gln Pro Gly
145                 150                 155                 160
His Gly Gly Pro Ile Ser Thr Ala Asn Tyr Ala Lys Ile Asn Gln Ala
                165                 170                 175
Tyr Gln Ile Ile Gln Lys Ala Leu Thr Ala Asn Glu Ala Asn Gly Asp
            180                 185                 190
Gly Val Pro Val Leu Ser Asp Thr Thr Lys Leu Asp Phe Thr Ile
        195                 200                 205
Gln Gly Asp Lys Arg Thr Gly Gly Arg Pro Asn Thr Pro Lys Lys Phe
    210                 215                 220
Pro Trp Ser Asp Gly Lys Tyr Ile His Thr Gln Trp Ile Asp Thr Thr
225                 230                 235                 240
Pro Gln Ser Thr Glu Thr Lys Ile Asn Thr Glu Asn Asn Ala Gln Glu
                245                 250                 255
Leu Leu Lys Gln Ala Ser Ile Ile Thr Thr Leu Asn Glu Ala Cys
            260                 265                 270
Pro Asn Phe Gln Asn Gly Gly Ser Gly Tyr Trp Gln Gly Ile Ser Gly
        275                 280                 285
Asn Gly Thr Met Cys Gly Met Phe Lys Asn Glu Ile Ser Ala Ile Gln
    290                 295                 300
Gly Met Ile Ala Asn Ala Gln Glu Ala Val Ala Gln Ser Lys Ile Val
305                 310                 315                 320
Ser Glu Asn Ala Gln Asn Gln Asn Asn Leu Asp Thr Gly Lys Pro Phe
                325                 330                 335
Asn Pro Phe Thr Asp Ala Ser Phe Ala Gln Ser Met Leu Lys Asn Ala
            340                 345                 350
Gln Ala Gln Ala Glu Ile Leu Asn Gln Ala Glu Gln Val Val Lys Asn
        355                 360                 365
Phe Glu Lys Ile Pro Lys Asn Phe Val Ser Asp Ser Leu Gly Val Cys
    370                 375                 380
Tyr Glu Glu Gln Gly Gly Glu Arg Arg Gly Thr Asn Pro Gly Gln Val
385                 390                 395                 400
Thr Ser Asn Thr Phe Ala Ser Gly Cys Ala Tyr Val Glu Gln Thr Ile
                405                 410                 415
Thr Asn Leu Asn Asn Ser Ile Ala His Phe Gly Thr Gln Glu Gln
            420                 425                 430
Ile Gln Gln Ala Glu Asn Ile Ala Asp Thr Leu Val Asn Phe Lys Ser
        435                 440                 445
Arg Tyr Ser Glu Leu Gly Asn Thr Tyr Asn Ser Ile Thr Thr Ala Leu
    450                 455                 460
Ser Lys Val Pro Asn Ala Gln Ser Leu Gln Asn Val Val Gly Lys Lys
465                 470                 475                 480
Asn Asn Pro Tyr Ser Pro Gln Gly Ile Glu Thr Asn Tyr Tyr Leu Asn
                485                 490                 495
Gln Asn Ser Tyr Asn Gln Ile Gln Thr Ile Asn Gln Glu Leu Gly Arg
            500                 505                 510
```

```
Asn Pro Phe Arg Lys Val Gly Ile Val Ser Ser Gln Thr Asn Asn Gly
        515                 520                 525
Ala Met Asn Gly Ile Gly Ile Gln Val Gly Tyr Lys Gln Phe Phe Gly
        530                 535                 540
Gln Lys Arg Lys Trp Gly Ala Arg Tyr Tyr Gly Phe Phe Asp Tyr Asn
545                 550                 555                 560
His Ala Phe Ile Lys Ser Ser Phe Phe Asn Ser Ala Ser Asp Val Trp
                565                 570                 575
Thr Tyr Gly Phe Gly Ala Asp Ala Leu Tyr Asn Phe Ile Asn Asp Lys
            580                 585                 590
Ala Thr Asn Phe Leu Gly Lys Asn Asn Lys Leu Ser Val Gly Leu Phe
        595                 600                 605
Gly Gly Ile Ala Leu Ala Gly Thr Ser Trp Leu Asn Ser Glu Tyr Val
    610                 615                 620
Asn Leu Ala Thr Met Asn Asn Val Tyr Asn Ala Lys Met Asn Val Ala
625                 630                 635                 640
Asn Phe Gln Phe Leu Phe Asn Met Gly Val Arg Met Asn Leu Ala Arg
                645                 650                 655
Ser Lys Lys Lys Gly Ser Asp His Ala Ala Gln His Gly Ile Glu Leu
                660                 665                 670
Gly Leu Lys Ile Pro Thr Ile Asn Thr Asn Tyr Tyr Ser Phe Met Gly
        675                 680                 685
Ala Glu Leu Lys Tyr Arg Arg Leu Tyr Ser Val Tyr Leu Asn Tyr Val
        690                 695                 700
Phe Ala Tyr
705

(2) INFORMATION FOR SEQ ID NO:5:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:5:

GAAGACGACG GCTTTTACAC AAGCGTAGGC TATCAAATCG GTGAAGCCGC TCAAATGGTA      60
```